(12) United States Patent
Chang et al.

(10) Patent No.: US 11,447,469 B2
(45) Date of Patent: Sep. 20, 2022

(54) HETERO RING-FUSED PHENYL COMPOUNDS FOR INHIBITING TNIK AND MEDICAL USES THEREOF

(71) Applicants: Korea Research Institute of Chemical Technology, Daejeon (KR); Industry-Academic Cooperation Foundation, Yonsei University, Seoul (KR)

(72) Inventors: Sung Youn Chang, Daejeon (KR); Hyuk Lee, Daejeon (KR); Ki Young Kim, Daejeon (KR); Bum Tae Kim, Daejeon (KR); Sung Soo Kim, Seoul (KR); Seong Hwan Kim, Daejeon (KR); Hwan Jung Lim, Daejeon (KR); Jung Nyoung Heo, Daejeon (KR); Sang Joon Shin, Seoul (KR); Sang Youn Park, Seoul (KR)

(73) Assignees: Korea Research Institute of Chemical Technology, Daejeon (KR); Industry-Academic Cooperation Foundation, Yonsei University, Seoul (KR)

( * ) Notice: Subject to any disclaimer, the term of this patent is extended or adjusted under 35 U.S.C. 154(b) by 62 days.

(21) Appl. No.: 16/967,825

(22) PCT Filed: Jan. 31, 2019

(86) PCT No.: PCT/KR2019/001403
§ 371 (c)(1),
(2) Date: Aug. 6, 2020

(87) PCT Pub. No.: WO2019/156438
PCT Pub. Date: Aug. 15, 2019

(65) Prior Publication Data
US 2021/0047300 A1    Feb. 18, 2021

(30) Foreign Application Priority Data
Feb. 7, 2018 (KR) .................. 10-2018-0015161

(51) Int. Cl.
*C07D 403/12* (2006.01)
*C07D 401/12* (2006.01)
*C07D 403/14* (2006.01)
*C07D 413/12* (2006.01)
*C07D 413/14* (2006.01)
*C07D 417/14* (2006.01)

(52) U.S. Cl.
CPC ......... *C07D 403/12* (2013.01); *C07D 401/12* (2013.01); *C07D 403/14* (2013.01); *C07D 413/12* (2013.01); *C07D 413/14* (2013.01); *C07D 417/14* (2013.01)

(58) Field of Classification Search
CPC .. C07D 403/12; C07D 401/12; C07D 403/14; C07D 413/12; C07D 413/14; C07D 417/14
See application file for complete search history.

(56) References Cited

U.S. PATENT DOCUMENTS

| 2004/0122237 | A1* | 6/2004 | Amiri | C07D 401/14 548/161 |
|---|---|---|---|---|
| 2010/0137386 | A1 | 6/2010 | Yamada et al. | |
| 2012/0165334 | A1* | 6/2012 | Boezio | C07D 405/14 544/324 |
| 2016/0289196 | A1 | 10/2016 | Choi et al. | |
| 2021/0047277 | A1* | 2/2021 | Chang | C07D 413/10 |

FOREIGN PATENT DOCUMENTS

| WO | WO 2006/004865 | 1/2006 |
|---|---|---|
| WO | WO 2019/156438 | 8/2019 |

OTHER PUBLICATIONS

Gupta; J. Chem. Sci., 2009, 121, 347-351. DOI: 10.1007/s12039-009-0040-9 (Year: 2009).*
Yamada; "Emergence of TNIK inhibitors in cancer therapeutics", Cancer Sci 2017, 108, 818-823. DOI: 10.1111/cas.13203 (Year: 2017).*
International Search Report and the Written Opinion dated May 13, 2019 From the International Searching Authority Re. Application No. PCT/KR2019/001403. (12 Pages).
Karthikeyan et al. "N-(1H-Pyrazol-3-Y1)Quinazolin-4-Amines as A Novel Class of Casein Kinase 1Delta/Epsilon Inhibitors: Synthesis, Biological Evaluation and Molecular Modeling Studies", Bioorganic & Medicinal Chemistry Letters, 27(12): 2663-2667, Available Online Apr. 27, 2017.
STN "6-Quinolinamine, N-[5-(4-Fluorophenyl)-1H-Pyrazol-3-Y1]-", STN Express, Chemical Abstract Compound. CAS Registry No. 916439-12-8. 13 P., Dec. 28, 2006.
Supplementary European Search Report and the European Search Opinion dated Oct. 21, 2021 From the European Patent Office Re. Application No. 19750420.2 (6 Pages).

* cited by examiner

*Primary Examiner* — Daniel R Carcanague
(74) *Attorney, Agent, or Firm* — Harness, Dickey & Pierce, P.L.C.

(57) ABSTRACT

The present disclosure provides the compound having inhibitory property against TNIK having a specific chemical structure or its pharmaceutically acceptable salt. The present disclosure also provides a composition comprising the compound or its pharmaceutically acceptable salt. The present disclosure also provides a medical use of the compound, its salt or the composition comprising the compound or its pharmaceutically acceptable salt for treating or preventing cancer. The present disclosure also provides a method of treatment or prevention of cancer comprising administering the compound, its salt or the composition comprising the compound or its salt to a subject in need of such treatment or prevention.

8 Claims, No Drawings

HETERO RING-FUSED PHENYL COMPOUNDS FOR INHIBITING TNIK AND MEDICAL USES THEREOF

RELATED APPLICATIONS

This application is a National Phase of PCT Patent Application No. PCT/KR2019/001403 having International filing date of Jan. 31, 2019, which claims the benefit of priority of Korean Patent Application No. 10-2018-0015161 filed on Feb. 7, 2018. The contents of the above applications are all incorporated by reference as if fully set forth herein in their entirety.

TECHNICAL FIELD

The present disclosure relates to a group of compounds having an activity inhibiting Traf2- and Nck-interacting kinase (TNIK). The present disclosure also relates to pharmaceutical compositions comprising the compound. The present disclosure relates to methods useful for treating specific diseases, including cancer or tumor, using the compound. That is, the present disclosure relates to medical-uses of those compounds according to the present disclosure for treating or preventing cancer or tumor.

BACKGROUND ART

It is well known that inhibitors of Traf2- and Nck-interacting kinase (TNIK) are useful for treating cancer (e.g., U.S. Patent Application Publication no. 2010/0216795). More concretely, it is known that TNIK is hyperactive in colorectal cancer, breast cancer, brain tumor, gastric cancer, liver cancer, ovarian cancer and so on (J. S. Boehm et al., Cell 129, 1065-1079, 2007). Specifically, TNIK plays an important role in the growth of colorectal cancer, and TNIK was reported to be a target that is able to control aberrant Wnt signaling in colorectal cancer (*Cancer Res* 2010; 70:5024-5033). TNIK gene was over-expressed in 7% of gastric cancer patients' tissue samples, and TNIK was reported to be a new target for treating gastric cancer (Oncogenesis 2014, 3, e89). In addition, TNIK was reported to be associated with proliferation and differentiation of leukemia stem cells in chronic myelogenous leukemia (The journal of clinical investigation 2012 122 624). In addition to these cancers or tumors, hepatocellular carcinoma, desmoid tumor, medulloblastoma (pediatric brain tumor), Wilms tumor (pediatric kidney cancer), thyroid tumor and so no is related to aberrant Wnt signaling, and thus medicine for these diseases can be developed based on TNIK inhibition.

Therefore, drugs inhibiting TNIK block the pathway of TNIK signaling, thereby inhibiting proliferation, survival, and angiogenesis of cancers. Drugs inhibiting TNIK thus are expected to be useful as medicine for treating cancer (See WO2010-100431 and WO2009-030890).

Meanwhile, TNIK inhibition was reported to be useful in treating chronic obstructive pulmonary disease (COPD), lupus nephritis, diabetic nephropathy, focal segmental glomerulosclerosis, renal fibrosis, Pulmonary fibrosis, scleroderma and so on.

Thus, TNIK inhibitors are expected to be useful in treating or preventing various diseases including inflammatory diseases as well as cancers.

DISCLOSURE OF INVENTION

Technical Problem

Thus one object of the present disclosure is to provide a compound having activity inhibiting TNIK (Traf2- and Nck-interacting kinase), pharmaceutical compositions comprising the compound as an effective agent, and medical-uses thereof for treating or preventing cancers.

Another object of the present disclosure is to provide a method for treating or ameliorating cancer comprising administering to a subject in need of treatment, amelioration or prevention of cancer a compound inhibiting TNIK activity according to the present disclosure.

Yet another object of the present disclosure is to provide a compound exhibiting synergic effect with other anticancer drugs by co-administration, pharmaceutical compositions comprising the compound as an effective agent, and medical uses thereof for treating or preventing cancer.

Yet another object of the present disclosure is to provide a method for treating or ameliorating cancer comprising administering to a subject in need of treatment, amelioration or prevention of cancer a compound inhibiting TNIK activity and anti-cancer drug having other mechanism simultaneously or sequentially.

Solution to Problem

Summary

To achieve the object, in one embodiment, there is provided a compound of Chemical Formula 1:

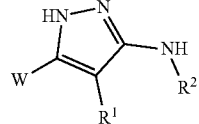

[Chemical Formula 1]

or a pharmaceutically acceptable salt thereof,
in the Chemical Formula 1
W is substituted or unsubstituted, aromatic ring, heteroaryl, or fused heteroaryl,
$R^1$ is H or F,
$R_2$ is hetero ring-fused phenyl unsubstituted or optionally substituted with $-C_{1-6}$ haloalkyl, $-C_{1-6}$alkyl, halogen, or $-C_{1-6}$alkoxy, wherein the hetero ring is fused with two adjacent carbon atoms of the phenyl.

In another embodiment, there is provided a pharmaceutical composition comprising a compound of Chemical Formula 1 or a pharmaceutically acceptable salt thereof, and a pharmaceutically-acceptable carrier or additive.

In various embodiments, the pharmaceutical composition further comprises one or more additional pharmaceutically active agents.

In yet another embodiment, there is provided a method for treating a condition comprising administering to a subject a therapeutically effective amount of a compound of Chemical Formula 1 or a pharmaceutically acceptable salt thereof, wherein the condition to be treated includes, but is not limited to, cancer such as colorectal cancer, breast cancer, brain tumor, gastric cancer, liver cancer, ovarian cancer, lung cancer, gastrointestinal cancer, leukemia, and melanoma, neoplasia, or tumor. The compound of Chemical Formula 1 or a pharmaceutically acceptable salt thereof according to the present disclosure is also useful in preventing metastasis and recurrence of tumor by targeting cancer stem cells. That is, there is provided medical-uses of the compound of Chemical Formula 1 or a pharmaceutically acceptable salt thereof for treating or preventing the diseases mentioned above.

In various embodiments, the method comprises administering combination agents of the compound of the present disclosure or its salt and other pharmaceutically active compounds. That is, there is provided a medical-use of combination medicine comprising the compound of the present disclosure or its pharmaceutically acceptable salt and other active agent for treating or preventing the diseases above.

The compounds, the pharmaceutical composition, and their medical use above are more fully described in the detailed description that follows.

DETAILED DESCRIPTION

The following description is merely exemplary in nature and is not intended to limit the present disclosure, application, or uses.

Definitions

The generic terms used in the present disclosure are herein defined for clarity.

This specification uses the terms "substituent", "radical", "group", "moiety", and "fragment" interchangeably.

As used herein, the term "patient" means an animal, preferably a mammal such as a non-primate (e.g., cow, horse, sheep, pig, chicken, turkey, quail, cat, dog, mouse, rat, rabbit or guinea pig) or a primate (e.g., monkey and human), most preferably a human.

As used herein, the term "alkyl" means a saturated straight chain or branched noncyclic hydrocarbon, unless the context clearly dictates otherwise, having from 1 to 10 carbon atoms. "lower alkyl" means alkyl having from 1 to 4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like.

As used herein, if the term "$C_{1-6}$" is used, it means the number of carbon atoms is from 1 to 6. For example, $C_{1-6}$ alkyl means an alkyl which carbon number is any integer of from 1 to 6.

The terms "halogen" and "halo" mean fluorine, chlorine, bromine or iodine.

As used herein, the term "haloalkyl", "haloalkoxy", "haloalkenyl" or "haloalkynyl" means an alkyl, alkoxy, alkenyl or alkynyl group, respectively, wherein one or more hydrogen atoms are substituted with halogen atoms. For example, the haloalkyl includes —$CF_3$, —$CHF_2$, —$CH_2F$, —$CBr_3$, —$CHBr_2$, —$CH_2Br$, —$CCl_3$, —$CHCl_2$, —$CH_2Cl$, —$CI_3$, —$CHI_2$, —$CH_2I$, —$CH_2$—$CF_3$, —$CH_2$—$CHF_2$, —$CH_2$—$CH_2F$, —$CH_2$—$CBr_3$, —$CH_2$—$CHBr_2$, —$CH_2$—$CH_2Br$, —$CH_2$—$CCl_3$, —$CH_2$—$CHCl_2$, —$CH_2$—$CH_2Cl$, —$CH_2$—$CI_3$, —$CH_2$—$CHI_2$, —$CH_2$—$CH_2I$, and the like, wherein alkyl and halogen are as described above.

The term "alkanoyl" or "acyl" means an —C(O)alkyl group, wherein alkyl is defined above, including —C(O)$CH_3$, —C(O)$CH_2CH_3$, —C(O)$(CH_2)_2CH_3$, —C(O)$(CH_2)_3CH_3$, —C(O)$(CH_2)_4CH_3$, —C(O)$(CH_2)_5CH_3$, and the like.

The term "alkanoyloxy" or "acyloxy" means an —OC(O)alkyl group, wherein alkyl is defined above, including —OC(O)$CH_3$, —OC(O)$CH_2CH_3$, —OC(O)$(CH_2)_2CH_3$, —OC(O)$(CH_2)_3CH_3$, —OC(O)$(CH_2)_4CH_3$, —OC(O)$(CH_2)_5$ $CH_3$, and the like.

The term "alkoxy" means an —O-(alkyl) group, wherein alkyl is defined above, including —$OCH_3$, —$OCH_2CH_3$, —O$(CH_2)_2CH_3$, —O$(CH_2)_3CH_3$, —O$(CH_2)_4CH_3$, —O$(CH_2)_5CH_3$, and the like.

The term "lower alkoxy" means —O-(lower alkyl), wherein lower alkyl is as described above.

The term "aryl" means a carbocyclic aromatic group containing from 5 to 10 ring atoms. Representative examples include, but are not limited to, phenyl, tolyl, xylyl, naphthyl, tetrahydronaphthyl, anthracenyl, fluorenyl, indenyl, and azulenyl. A carbocyclic aromatic group can be unsubstituted or optionally substituted.

The term "aryloxy" is RO—, where R is aryl as defined above. "arylthio" is RS—, where R is aryl as defined above.

The term "cycloalkyl" means a monocyclic or polycyclic saturated ring having carbon and hydrogen atoms and having no carbon-carbon multiple bonds. Examples of cycloalkyl groups include, but are not limited to, ($C_3$-$C_7$)cycloalkyl groups, including cyclopropyl, cyclobutyl, cyclopentyl, cyclohexyl, and cycloheptyl. A cycloalkyl group can be unsubstituted or optionally substituted. In one embodiment, the cycloalkyl group is a monocyclic ring or bicyclic ring.

The term "mono-alkylamino" means —NH(alkyl), wherein alkyl is defined above, such as —$NHCH_3$, —$NHCH_2CH_3$, —NH$(CH_2)_2CH_3$, —NH$(CH_2)_3CH_3$, —NH$(CH_2)_4CH_3$, —NH$(CH_2)_5CH_3$, and the like.

The term "di-alkylamino" means —N(alkyl)(alkyl), wherein each alkyl is independently an alkyl group as defined above, including —N$(CH_3)_2$, —N$(CH_2CH_3)_2$, —N$((CH_2)_2CH_3)_2$, —N$(CH_3)(CH_2CH_3)$, and the like.

The term "alkylamino" means mono-alkylamino or di-alkylamino as defined above.

The term "carboxyl" and "carboxy" mean —COOH.

The term "aminoalkyl" means -(alkyl)-$NH_2$, wherein alkyl is defined above, including —$CH_2$—$NH_2$, —$(CH_2)_2$—$NH_2$, —$(CH_2)_3$—$NH_2$, —$(CH_2)$—$NH_2$, —$(CH_2)_5$—$NH_2$ and the like.

The term "mono-alkylaminoalkyl" means -(alkyl)-NH(alkyl), wherein each alkyl is independently an alkyl group defined above, including —$CH_2$—NH—$CH_3$, —$CH_2$—$NHCH_2CH_3$, —$CH_2$—NH$(CH_2)_2CH_3$, —$CH_2$—NH$(CH_2)_3$ $CH_3$, —$CH_2$—NH$(CH_2)_4CH_3$, —$CH_2$—NH$(CH_2)_5CH_3$, —$(CH_2)_2$—NH—$CH_3$, and the like.

The term "heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl.

The term "heterocycle" means a 5- to 7-membered monocyclic, or 7- to 10-membered bicyclic, heterocyclic ring which is either saturated, unsaturated, and which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined above. Representative heterocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, and tetrahydrothiopyranyl.

The term "heterocycle fused to phenyl" means a heterocycle, wherein heterocycle is defined as above, that is attached to a phenyl ring at two adjacent carbon atoms of the phenyl ring.

The term "hydroxyalkyl" means alkyl, wherein alkyl is as defined above, having one or more hydrogen atoms replaced with hydroxy, including —$CH_2OH$, —$CH_2CHOH$, —(CH)CHOH, —$(CH_2)_3CH_2OH$, —$(CH_2)_4CH_2OH$, —$(CH_2)_5CH_2OH$, —CH(OH)—$CH_3$, —$CH_2CH(OH)CH_3$, and the like.

The term "sulfonyl" means —$SO_3H$.

The term "sulfonylalkyl" means —$SO_2$-(alkyl), wherein alkyl is defined above, including —SO—$CH_3$, —SO—$CH_2CH_3$, —SO—$(CH_2)_2CH_3$, —SO—$(CH_2)_3CH_3$, —$SO_2$—$(CH_2)_4CH_3$, —SO—$(CH_2)_5CH_3$, and the like.

The term "sulfinylalkyl" means —SO-(alkyl), wherein alkyl is defined above, including —SO—$CH_3$, —SO—$CH_2CH_3$, —SO—$(CH_2)_2CH_3$, —SO—$(CH_2)_3CH_3$, —SO—$(CH_2)_4CH_3$, —SO—$(CH_2)_5CH_3$, and the like.

The term "thioalkyl" means —S-(alkyl), wherein alkyl is defined above, including —S—$CH_3$, —S—$CH_2CH_3$, —S—$(CH_2)_2CH_3$, —S—$(CH_2)_3CH_3$, —S—$(CH_2)_4CH_3$, —S—$(CH_2)_3CH_3$, and the like.

As used herein, the term "substituted" means any of the above groups (i.e., alkyl, aryl, heteroaryl, heterocycle or cycloalkyl) wherein at least one hydrogen atom of the moiety being substituted is replaced with a substituent. In one embodiment, each carbon atom of the group being substituted is substituted with no more than two substituents. In another embodiment, each carbon atom of the group being substituted is substituted with no more than one substituent. In the case of a keto substituent, two hydrogen atoms are replaced with an oxygen which is attached to the carbon via a double bond. Unless specifically defined, substituents include halogen, hydroxyl, (lower) alkyl, haloalkyl, mono- or di-alkylamino, aryl, heterocycle, —$NO_2$, —$NR_aR_b$, —$NR_aC(=O)R_b$, —$NR_aC(=O)NR_aR_b$, —$NR_aC(=O)OR_b$, —$NR_aSO_2R_b$, —$OR_a$, —CN, —$C(=O)R_a$, —$C(=O)OR_a$, —$C(=O)NR_aR_b$, —OC(=O)$R_a$, —OC(=O)$OR_a$, —OC(=O)$NR_aR_b$, —$NR_aSO_2R_b$, —$PO_3R_a$, —PO($OR_a$)($OR_b$), —$SO_2R_a$, —S(O)$R_a$, —SO(N)$R_a$ (e.g., sulfoximine), —($R_a$)S=$NR_b$ (e.g., sulfilimine) and —$SR_a$, wherein $R_a$ and $R_b$ are the same or different and independently hydrogen, halogen, amino, alkyl, haloalkyl, aryl or heterocycle, or wherein $R_a$ and $R_b$ taken together with the nitrogen atom to which they are attached form a heterocycle. $R_a$ and $R_b$ may be in the plural based on atoms which those are attached to.

As used herein, the term "pharmaceutically acceptable salt(s)" refers to a salt prepared from active compounds according to the present disclosure with relatively non-toxic acids or bases with active compounds, depending on the particular substituents of those compounds. When the compounds have a relatively acidic group, base-added salts can be obtained by contacting the neutral compounds with a sufficient amount of the desired base and a pure or inert solvent. Suitable pharmaceutically acceptable base addition salts include, but are not limited to sodium, potassium, calcium, aluminum, organic amino, magnesium salts and the like. When the compounds have a relatively basic group, acid-added salts can be obtained by contacting the neutral compounds with a sufficient amount of the desired acid and pure or inert solvent. Suitable pharmaceutically acceptable acid addition salts include salts derived from non-toxic organic acids including, but are not limited to, acetic acid, propionic acid, isobutyl acid, oxalic acid, maleic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, and the like, and non-toxic inorganic acids including, but are not limited to, hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydrogen iodide, phosphorous acid and the like. Also it includes a salt of amino acid such as arginate or its analogues, and it also includes analogues of organic acid such as glucuronic or galacturonic acid. Some specific compounds of this disclosure have both basic and acidic functionality for the conversion of compounds with a basic or acidic portion (addition) salts. Other examples of salts are disclosed in well-known literature on the art, for example, *Remington's Pharmaceutical Sciences*, $18^{th}$ eds., Mack Publishing, Easton Pa. (1990) or *Remington: The Science and Practice of Pharmacy*, $19^{th}$ eds, are disclosed in Mack Publishing, Easton Pa. (1995).

As used herein, the term "effective amount" includes that amount of a compound of this disclosure sufficient to destroy, modify, control or remove a primary, regional or metastatic cancer cell or tissue; delay or minimize the spread of cancer; or provide a therapeutic benefit in the treatment or management of cancer, a neoplastic disorder, or tumor. An "effective amount" also includes the amount of a compound of this disclosure sufficient to result in cancer or neoplastic cell death. An "effective amount" also includes the amount of a compound of this disclosure sufficient to inhibit or decrease TNIK activity either in vitro or in vivo.

As used herein, the term "prophylactically effective amount" refers to the amount of a compound sufficient to prevent the recurrence or spread of cancer or the occurrence of cancer in a patient, including but not limited to those predisposed to cancer or previously exposed to a carcinogen.

As used herein, the term "neoplastic" means an abnormal growth of a cell or tissue (e.g., a tumor) which may be benign or cancerous.

As used herein, the term "prevention" includes the prevention of the recurrence, spread or onset of cancer in a patient.

As used herein, the term "treatment" includes the eradication, removal, modification, or control of primary, regional, or metastatic cancer tissue; and the minimizing or delay of the spread of cancer.

As used herein, the phrase "Compound(s) of this/the Disclosure" includes any compound(s) of Chemical Formula 1, as well as clathrates, hydrates, solvates, or polymorphs thereof. And, even if the term "Compound(s) of the Disclosure" does not mention its pharmaceutically acceptable sat, the term includes salts thereof. In one embodiment, the compounds of this disclosure include stereo-chemically pure compounds, e.g., those substantially free (e.g., greater than 85% ee, greater than 90% ee, greater than 95% ee, greater than 97% ee, or greater than 99% ee) of other stereoisomers. That is, if the compounds of Chemical Formula 1 according to the present disclosure or salts thereof are tautomeric isomers and/or stereoisomers (e.g., geometrical isomers and conformational isomers), such isolated isomers and their mixtures also are included in the scope of this disclosure. If the compounds of the present disclosure or salts thereof have an asymmetric carbon in their structures, their active optical isomers and their racemic mixtures also are included in the scope of this disclosure.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and/or acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

If any compound (prodrug) produces the compound or its salt of this disclosure after degrading in vivo, such compound is included in this disclosure. As used herein and unless otherwise indicated, the term "prodrug" means a compound that can hydrolyze, oxidize, or otherwise react under biological conditions (in vitro or in vivo) to provide an active compound, particularly a compound of this disclosure. Examples of prodrugs include, but are not limited to, metabolites of a compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6$^{th}$ ed. (Donald J. Abraham ed., 2001, Wiley) and *Design and Application of Prodrugs* (H. Bundgaard ed., 1985, Harwood Academic Publishers Gmfh).

As used herein, the term "purified" means that when isolated, the isolate is greater than 90% pure, in one embodiment greater than 95% pure, in another embodiment greater than 99% pure and in another embodiment greater than 99.9% pure.

The term "hydrido" means a single —H atom (H) and may be used interchangeably with the symbol "H" or the term "hydrogen".

If a substituent is described as being "optionally substituted," the substituent may be either (1) not substituted or (2) substituted. If a substitutable position is not substituted, the default substituent is a hydrido radical.

As used herein, the singular forms "a" and "an" may include plural reference unless the context clearly dictates otherwise.

The term "pharmaceutically-acceptable" means suitable for use in pharmaceutical preparations, generally considered as safe for such use, officially approved by a regulatory agency of a national or state government for such use, or being listed in South Korea or the U. S. Pharmacopoeia or other generally recognized pharmacopoeia for use in animals, and more particularly in humans.

Compounds of the Present Disclosure

There is provided a compound of Chemical Formula 1:

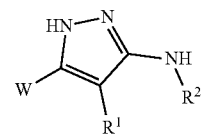

[Chemical Formula 1]

or a pharmaceutically acceptable salt thereof,
in the Chemical Formula 1
W is substituted or unsubstituted, aromatic ring, heteroaryl, or fused heteroaryl,
$R^1$ is H or F,
$R_2$ is hetero ring-fused phenyl unsubstituted or optionally substituted with —$C_{1-6}$ haloalkyl, —$C_{1-6}$alkyl, halogen, or —$C_{1-6}$alkoxy, wherein the hetero ring is fused with two adjacent carbon atoms of the phenyl.

The hetero ring-fused phenyl includes indoline, 3H-indole, 1H-indole, 2H-isoindole, 1H-indazole, benzimidazole, benzofuran, isobenzofuran, benzo[c]thiophene, benzo[b]thiophene, benzo[d]isoxazole, benzo[c]isoxazole, benzo[d]isothiazole, benzo[c]isothiazole, benzo[d]oxazole, benzo[d]thiazole, benzo[c][1,2,5]thiadiazole, 1,2-benzisothiazole-3(2H)-one, 1,2,3,4-tetrahydroquinoline, 1,2-dihydroquinoline, 1,2-dihydroisoquinoline, quinoline, isoquinoline, quinoxaline, phthalazine, quinazoline, cinnoline, 2H-chromene, 1H-isochromene, 3H-isochromene, 2H-chromene-2-one, 2H-benzo[e][1,2]oxazine, 2H-benzo[e][1,3]oxazine, 2H-benzo[b][1,4]oxazine, quinolin-2(1H)-one, isoquinolin-1(2H)-one, 1,3-dihydro-2H-benzo[d]imidazol-2-one, 3,4-dihydroquinolin-2(1H)-one, indolin-2-one, benzo[b][1,4]oxazin-3(4H)-one, benzo[d]oxazol-2(3H)-one, 1H-benzo[d]imidazole, 1,3-dihydro-2H-benzo[d]imidazole-2-thione, and benzo[d]thiazol-2(3H)-one.

In yet another embodiment, preferably,
in the Chemical Formula 1
W is substituted or unsubstituted, phenyl, pyridyl, thiophene, thiazole, pyrrole, benzothiophene, indole, oxazole, pyrazole, imidazole, pyrimidine, benzopyrazole, benzothiazole, benzoxazole, benzoimidazole, or benzothiophene, $R^1$ is H or F, $R^2$ is indoline, 3H-indole, 1H-indole, 2H-isoindole, 1H-indazole, benzimidazole, benzofuran, isobenzofuran, benzo[c]thiophene, benzo[b]thiophene, benzo[d]isoxazole, benzo[c]isoxazole, benzo[d]isothiazole, benzo[c]isothiazole, benzo[d]oxazole, benzo[d]thiazole, benzo[c][1,2,5]thiadiazole, 1,2-benzisothiazole-3(2H)-one, 1,2,3,4-tetrahydroquinoline, 1,2-dihydroquinoline, 1,2-dihydroisoquinoline, quinoline, isoquinoline, quinoxaline, phthalazine, quinazoline, cinnoline, 2H-chromene, 1H-isochromene, 3H-isochromene, 2H-chromene-2-one, 2H-benzo[e][1,2]oxazine, 2H-benzo[e][1,3]oxazine, 2H-benzo[b][1,4]oxazine, quinolin-2(1H)-one, isoquinolin-1(2H)-one, 1,3-dihydro-2H-benzo[d]imidazol-2-one, 3,4-dihydroquinolin-2(1H)-one, indolin-2-one, benzo[b][1,4]oxazin-3(4H)-one, benzo[d]oxazol-2(3H)-one, 1H-benzo[d]imidazole, 1,3-dihydro-2H-benzo[d]imidazole-2-thione, or benzo[d]thiazol-2(3H)-one, unsubstituted or substituted with —$C_{1-6}$haloalkyl, —$C_{1-6}$alkyl, halogen, or —$C_{1-6}$alkoxy.

In yet another embodiment, more preferably, in the Chemical Formula 1,

W is substituted or unsubstituted, phenyl, pyridyl, thiophene, thiazole, pyrrole, benzothiophene, or indole, $R^1$ is H or F, $R_2$ is 1H-indole, 1H-indazole, 1,3-dihydro-2H-benzo[d]imidazol-2-one, 3,4-dihydroquinolin-2(1H)-one, indolin-2-one, benzo[b][1,4]oxazin-3(4H)-one, benzo[d]oxazol-2(3H)-one, 2-methyl-1H-benzo[d]imidazole, 4-methylquinolin-2(1H)-one, 1,3-dihydro-2H-benzo[d]imidazole-2-thione, benzo[d]thiazol-2(3H)-one, 4-methyl-1H-indazol, 6-methyl-1H-indazol, 4-methyl-1H-benzo[d]imidazole, or 6-methyl-1H-benzo[d]imidazole, or 1H-benzo[d]imidazole.

The inventors had synthesized and evaluated lots of compounds to find out compounds having good TNIK inhibition activity and high selectivity against TNIK, thereby having good inhibition effect against cancer cells and low side effects about normal cells. Finally, the compounds of the present disclosure are identified to be suitable for the object of the present disclosure.

Non-limiting examples of the compounds of the present disclosure include the compounds of Table 1 below and pharmaceutically acceptable salts thereof.

TABLE 1

| Compound No. | Structure | Name |
| --- | --- | --- |
| 1 | 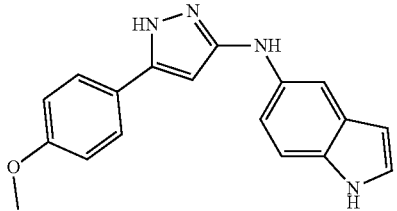 [SMILES: COc1ccc(-c2cc(Nc3ccc4[nH]ccc4c3)n[nH]2)cc1] | N-(5-(4-methoxyphenyl)-1H-pyrazol-3-yl)-1H-indol-5-amine |
| 2 | 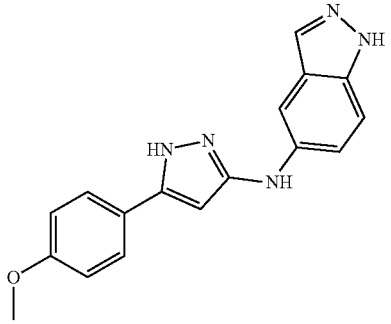 [SMILES: COc1ccc(-c2cc(Nc3ccc4[nH]ncc4c3)n[nH]2)cc1] | N-(5-(4-methoxyphenyl)-1H-pyrazol-3-yl)-1H-indazol-5-amine |
| 3 | 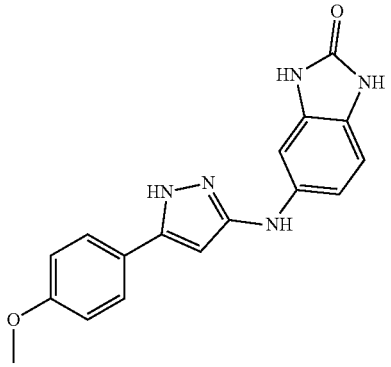 [SMILES: COc1ccc(-c2cc(Nc3ccc4[nH]c(=O)[nH]c4c3)n[nH]2)cc1] | 5-((5-(4-methoxyphenyl)-1H-pyrazol-3-yl)amino)-1,3-dihydro-2H-benzo[d]imidazol-2-one |

TABLE 1-continued
| Compound No. | Structure | Name |
|---|---|---|
| 4 | 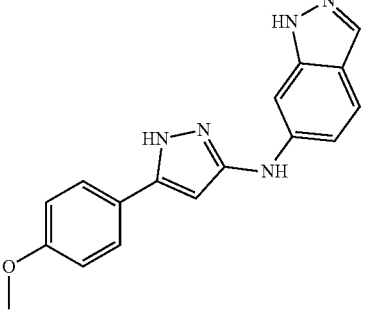 | N-(5-(4-methoxyphenyl)-1H-pyrazol-3-yl)-1H-indazol-6-amine |
| 5 | 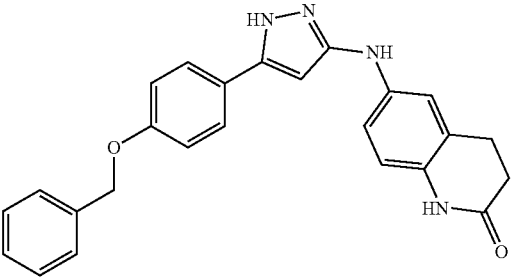 [SMILES: O=C1CCc2cc(Nc3cc(-c4ccc(OCc5ccccc5)cc4)[nH]n3)ccc2N1] | 6-((5-(4-(benzyloxy)phenyl)-1H-pyrazol-3-yl)amino)-3,4-dihydroquinolin-2(1H)-one |
| 6 | 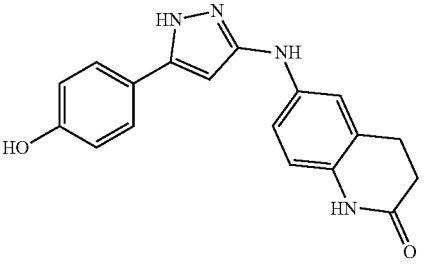 [SMILES: O=C1CCc2cc(Nc3cc(-c4ccc(O)cc4)[nH]n3)ccc2N1] | 6-((5-(4-hydroxyphenyl)-1H-pyrazol-3-yl)amino)-3,4-dihydroquinolin-2(1H)-one |
| 7 | 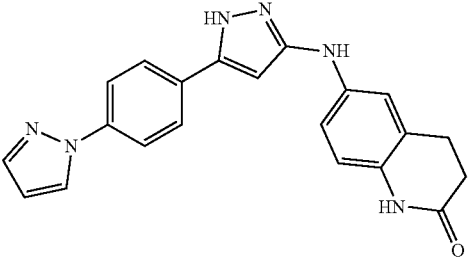 [SMILES: O=C1CCc2cc(Nc3cc(-c4ccc(-n5cccn5)cc4)[nH]n3)ccc2N1] | 6-((5-(4-(1H-pyrazol-1-yl)phenyl)-1H-pyrazol-3-yl)amino)-3,4-dihydroquinolin-2(1H)-one |
| 8 | 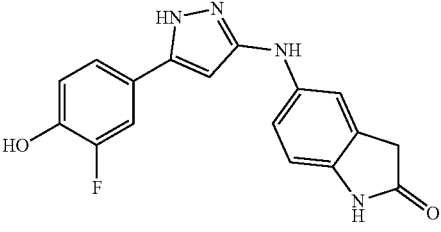 [SMILES: O=C1Cc2cc(Nc3cc(-c4ccc(O)c(F)c4)[nH]n3)ccc2N1] | 5-((5-(3-fluoro-4-hydroxyphenyl)-1H-pyrazol-3-yl)amino)indolin-2-one |

TABLE 1-continued

| Compound No. | Structure | Name |
|---|---|---|
| 9 | 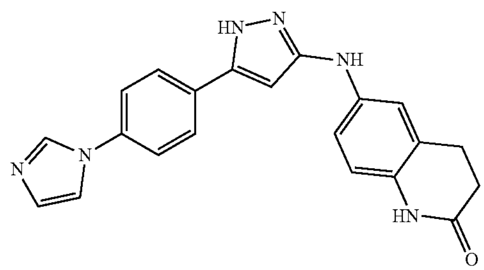 [SMILES: O=C1CCc2cc(Nc3cc(-c4ccc(-n5ccnc5)cc4)[nH]n3)ccc2N1] | 6-((5-(4-(1H-imidazol-1-yl)phenyl)-1H-pyrazol-3-yl)amino)-3,4-dihydroquinolin-2(1H)-one |
| 10 | 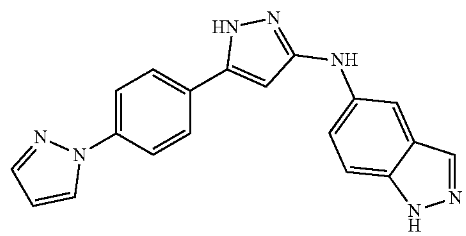 [SMILES: c1cnn(-c2ccc(-c3cc(Nc4ccc5[nH]ncc5c4)n[nH]3)cc2)c1] | N-(5-(4-(1H-pyrazol-1-yl)phenyl)-1H-pyrazol-3-yl)-1H-indazol-5-amine |
| 11 | 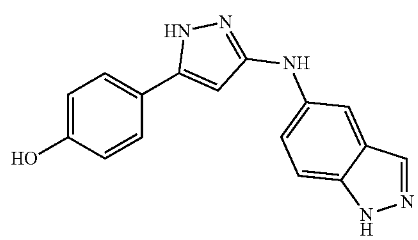 [SMILES: Oc1ccc(-c2cc(Nc3ccc4[nH]ncc4c3)n[nH]2)cc1] | 4-(3-((1H-indazol-5-yl)amino)-1H-pyrazol-5-yl)phenol |
| 12 | 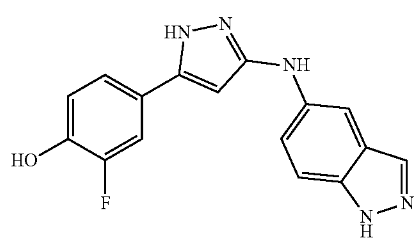 [SMILES: Oc1ccc(-c2cc(Nc3ccc4[nH]ncc4c3)n[nH]2)cc1F] | 4-(3-((1H-indazol-5-yl)amino)-1H-pyrazol-5-yl)-2-fluorophenol |
| 13 | 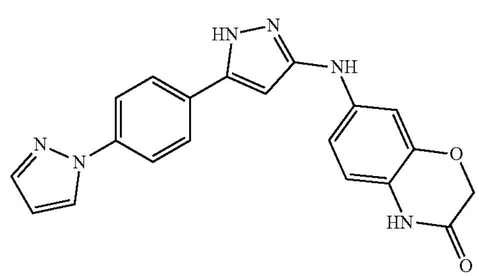 [SMILES: O=C1COc2cc(Nc3cc(-c4ccc(-n5cccn5)cc4)[nH]n3)ccc2N1] | 7-((5-(4-(1H-pyrazol-1-yl)phenyl)-1H-pyrazol-3-yl)amino)-2H-benzo[b][1,4]oxazin-3(4H)-one |
| 14 | 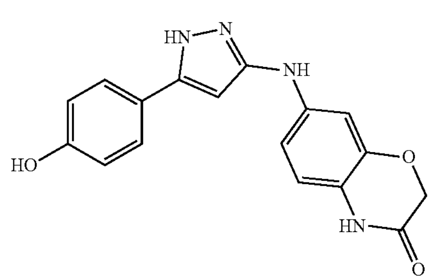 [SMILES: O=C1COc2cc(Nc3cc(-c4ccc(O)cc4)[nH]n3)ccc2N1] | 7-((5-(4-hydroxyphenyl)-1H-pyrazol-3-yl)amino)-2H-benzo[b][1,4]oxazin-3(4H)-one |

TABLE 1-continued

| Compound No. | Structure | Name |
|---|---|---|
| 15 | 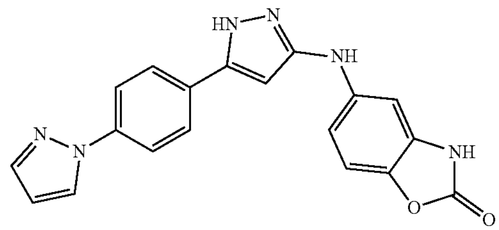 [SMILES: O=c1[nH]c2cc(Nc3cc(-c4ccc(-n5cccn5)cc4)[nH]n3)ccc2o1] | 5-((5-(4-(1H-pyrazol-1-yl)phenyl)-1H-pyrazol-3-yl)amino)benzo[d]oxazol-2(3H)-one |
| 16 | 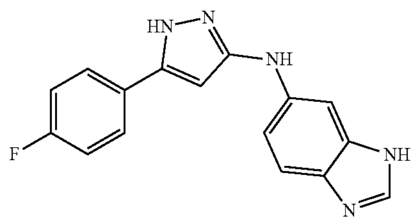 [SMILES: Fc1ccc(-c2cc(Nc3ccc4nc[nH]c4c3)n[nH]2)cc1] | N-(5-(4-fluorophenyl)-1H-pyrazol-3-yl)-1H-benzo[d]imidazol-6-amine |
| 17 | 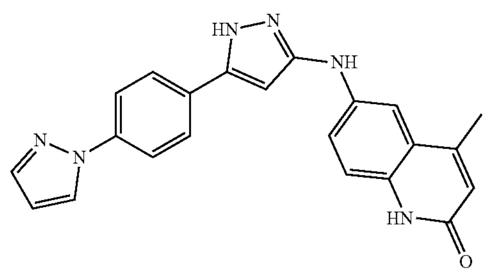 [SMILES: Cc1cc(=O)[nH]c2ccc(Nc3cc(-c4ccc(-n5cccn5)cc4)[nH]n3)cc12] | 6-((5-(4-(1H-pyrazol-1-yl)phenyl)-1H-pyrazol-3-yl)amino)-4-methylquinolin-2(1H)-one |
| 18 | 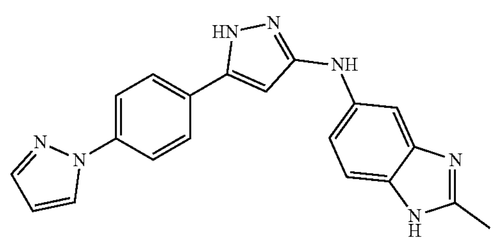 [SMILES: Cc1nc2cc(Nc3cc(-c4ccc(-n5cccn5)cc4)[nH]n3)ccc2[nH]1] | N-(5-(4-(1H-pyrazol-1-yl)phenyl)-1H-pyrazol-3-yl)-2-methyl-1H-benzo[d]imidazol-5-amine |
| 19 | 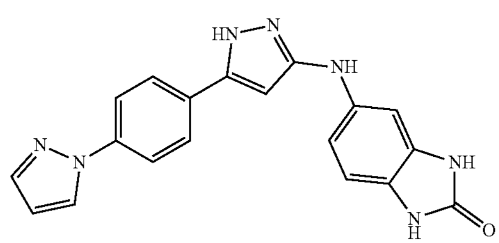 [SMILES: O=c1[nH]c2ccc(Nc3cc(-c4ccc(-n5cccn5)cc4)[nH]n3)cc2[nH]1] | 5-((5-(4-(1H-pyrazol-1-yl)phenyl)-1H-pyrazol-3-yl)amino)-1,3-dihydro-2H-benzo[d]imidazole-2-thione |
| 20 | 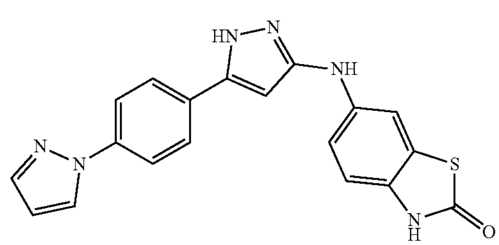 [SMILES: O=c1[nH]c2ccc(Nc3cc(-c4ccc(-n5cccn5)cc4)[nH]n3)cc2s1] | 6-((5-(4-(1H-pyrazol-1-yl)phenyl)-1H-pyrazol-3-yl)amino)benzo[d]thiazol-2(3H)-one |

TABLE 1-continued

| Compound No. | Structure | Name |
|---|---|---|
| 21 | 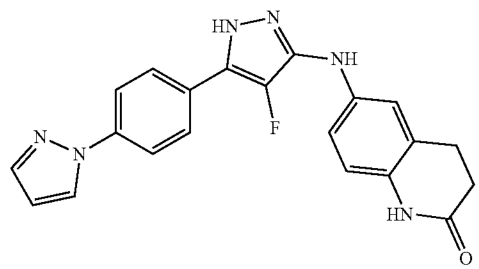 [SMILES: O=C1CCc2cc(Nc3n[nH]c(-c4ccc(-n5cccn5)cc4)c3F)ccc2N1] | 6-((5-(4-(1H-pyrazol-1-yl)phenyl)-4-fluoro-1H-pyrazol-3-yl)amino)-3,4-dihydroquinolin-2(1H)-one |
| 22 | 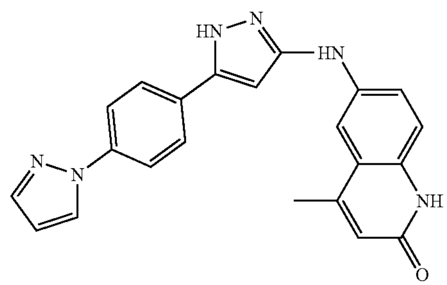 [SMILES: Cc1cc(=O)[nH]c2ccc(Nc3cc(-c4ccc(-n5cccn5)cc4)[nH]n3)cc12] | 6-((5-(4-(1H-pyrazol-1-yl)phenyl)-1H-pyrazol-3-yl)amino)-4-methylquinolin-2(1H)-one |
| 23 | 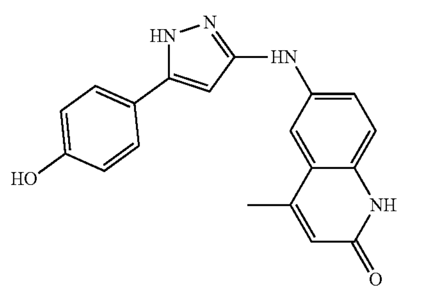 [SMILES: Cc1cc(=O)[nH]c2ccc(Nc3cc(-c4ccc(O)cc4)[nH]n3)cc12] | 6-((5-(4-hydroxyphenyl)-1H-pyrazol-3-yl)amino)-4-methylquinolin-2(1H)-one |
| 24 | 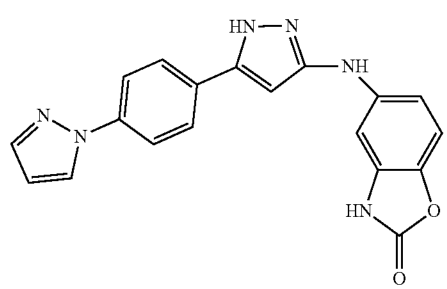 [SMILES: O=c1[nH]c2cc(Nc3cc(-c4ccc(-n5cccn5)cc4)[nH]n3)ccc2o1] | 5-((5-(4-(1H-pyrazol-1-yl)phenyl)-1H-pyrazol-3-yl)amino)benzo[d]oxazol-2(3H)-one |
| 25 | 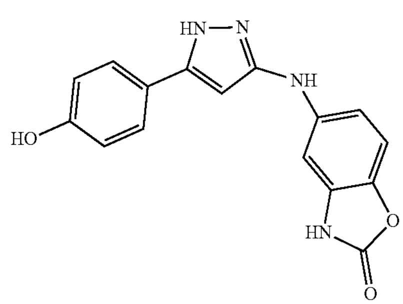 [SMILES: O=c1[nH]c2cc(Nc3cc(-c4ccc(O)cc4)[nH]n3)ccc2o1] | 5-((5-(4-hydroxyphenyl)-1H-pyrazol-3-yl)amino)benzo[d]oxazol-2(3H)-one |

TABLE 1-continued

| Compound No. | Structure | Name |
|---|---|---|
| 26 | 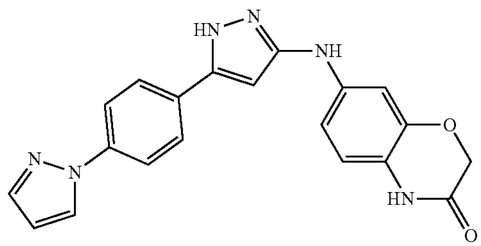 [SMILES: O=C1COc2cc(Nc3cc(-c4ccc(-n5cccn5)cc4)[nH]n3)ccc2N1] | 7-((5-(4-(1H-pyrazol-1-yl)phenyl)-1H-pyrazol-3-yl)amino)-2H-benzo[b][1,4]oxazin-3(4H)-one |
| 27 | 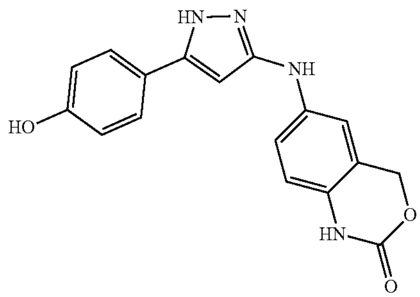 [SMILES: O=C1Nc2ccc(Nc3cc(-c4ccc(O)cc4)[nH]n3)cc2CO1] | 7-((5-(4-hydroxyphenyl)-H-pyrazol-3-yl)amino)-2H-benzo[b][1,4]oxazin-3(4H)-one |
| 28 | 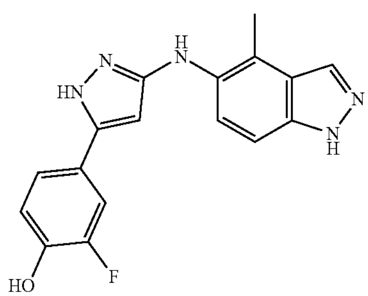 [SMILES: Cc1c(Nc2cc(-c3ccc(O)c(F)c3)[nH]n2)ccc2[nH]ncc12] | 2-fluoro-4-(3-((4-methyl-1H-indazol-5-yl)amino)-1H-pyrazol-5-yl)phenol |
| 29 | 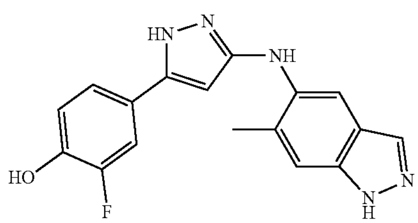 [SMILES: Cc1cc2[nH]ncc2cc1Nc1cc(-c2ccc(O)c(F)c2)[nH]n1] | 2-fluoro-4-(3-((6-methyl-1H-indazol-5-yl)amino)-1H-pyrazol-5-yl)phenol |
| 30 | 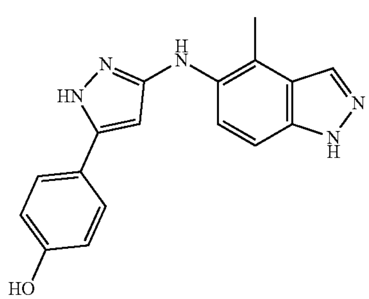 [SMILES: Cc1c(Nc2cc(-c3ccc(O)cc3)[nH]n2)ccc2[nH]ncc12] | 4-(3-((4-methyl-1H-indazol-5-yl)amino)-1H-pyrazol-5-yl)phenol |
| 31 | 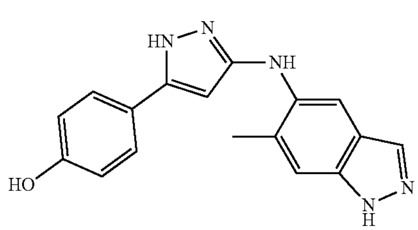 [SMILES: Cc1cc2[nH]ncc2cc1Nc1cc(-c2ccc(O)cc2)[nH]n1] | 4-(3-((6-methyl-1H-indazol-5-yl)amino)-1H-pyrazol-5-yl)phenol |

TABLE 1-continued

| Compound No. | Structure | Name |
| --- | --- | --- |
| 32 | 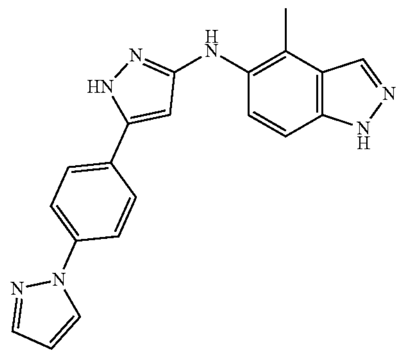 [SMILES: Cc1c(Nc2cc(-c3ccc(-n4cccn4)cc3)[nH]n2)ccc2[nH]ncc12] | N-(5-(4-(1H-pyrazol-1-yl)phenyl)-1H-pyrazol-3-yl)-4-methyl-1H-indazol-5-amine |
| 33 | 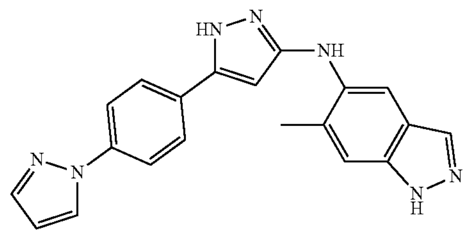 [SMILES: Cc1cc2[nH]ncc2cc1Nc1cc(-c2ccc(-n3cccn3)cc2)[nH]n1] | N-(5-(4-(1H-pyrazol-1-yl)phenyl)-1H-pyrazol-3-yl)-6-methyl-1H-indazol-5-amine |
| 34 | 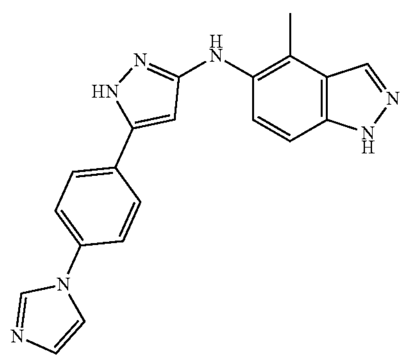 [SMILES: Cc1c(Nc2cc(-c3ccc(-n4ccnc4)cc3)[nH]n2)ccc2[nH]ncc12] | N-(5-(4-(1H-imidazol-1-yl)phenyl)-1H-pyrazol-3-yl)-4-methyl-1H-indazol-5-amine |
| 35 | 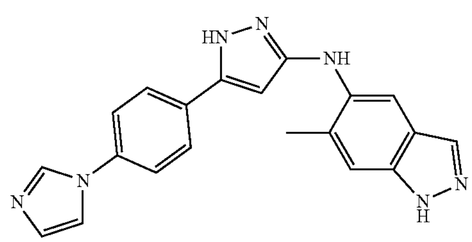 [SMILES: Cc1cc2[nH]ncc2cc1Nc1cc(-c2ccc(-n3ccnc3)cc2)[nH]n1] | N-(5-(4-(1H-imidazol-1-yl)phenyl)-1H-pyrazol-3-yl)-6-methyl-1H-indazol-5-amine |
| 36 | 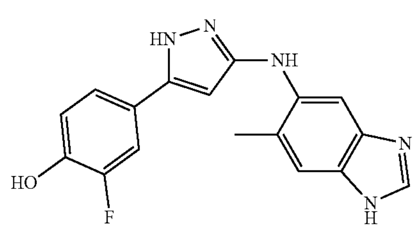 [SMILES: Cc1cc2[nH]cnc2cc1Nc1cc(-c2ccc(O)c(F)c2)[nH]n1] | 2-fluoro-4-(3-((6-methyl-1H-benzo[d]imidazol-5-yl)amino)-1H-pyrazol-5-yl)phenol |

TABLE 1-continued

| Compound No. | Structure | Name |
|---|---|---|
| 37 | 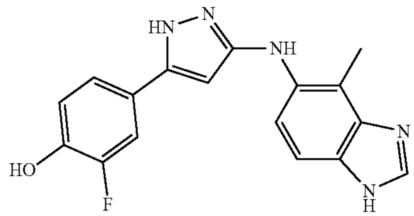 [SMILES: Cc1c(Nc2cc(-c3ccc(O)c(F)c3)[nH]n2)ccc2[nH]cnc12] | 2-fluoro-4-(3-((4-methyl-1H-benzo[d]imidazol-5-yl)amino)-1H-pyrazol-5-yl)phenol |
| 38 | 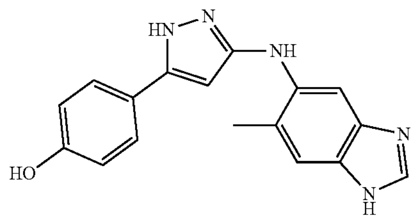 [SMILES: Cc1cc2[nH]cnc2cc1Nc1cc(-c2ccc(O)cc2)[nH]n1] | 4-(3-((6-methyl-1H-benzo[d]imidazol-5-yl)amino)-1H-pyrazol-5-yl)phenol |
| 39 | 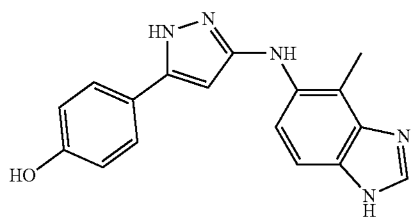 [SMILES: Cc1c(Nc2cc(-c3ccc(O)cc3)[nH]n2)ccc2[nH]cnc12] | 4-(3-((4-methyl-1H-benzo[d]imidazol-5-yl)amino)-1H-pyrazol-5-yl)phenol |
| 40 | 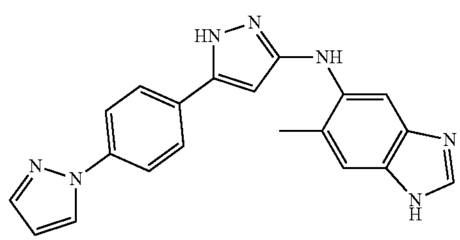 [SMILES: Cc1cc2[nH]cnc2cc1Nc1cc(-c2ccc(-n3cccn3)cc2)[nH]n1] | N-(5-(4-(1H-pyrazol-1-yl)phenyl)-1H-pyrazol-3-yl)-6-methyl-1H-benzo[d]imidazol-5-amine |
| 41 | 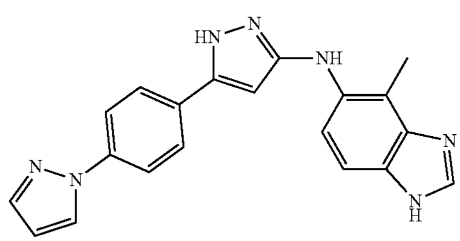 [SMILES: Cc1c(Nc2cc(-c3ccc(-n4cccn4)cc3)[nH]n2)ccc2[nH]cnc12] | N-(5-(4-(1H-pyrazol-1-yl)phenyl)-1H-pyrazol-3-yl)-4-methyl-1H-benzo[d]imidazol-5-amine |
| 42 | 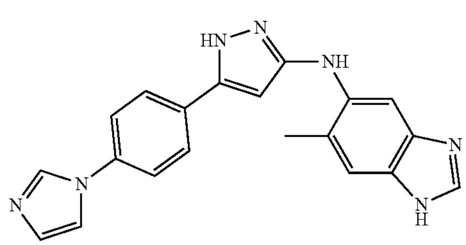 [SMILES: Cc1cc2[nH]cnc2cc1Nc1cc(-c2ccc(-n3ccnc3)cc2)[nH]n1] | N-(5-(4-(1H-imidazol-1-yl)phenyl)-1H-pyrazol-3-yl)-6-methyl-1H-benzo[d]imidazol-5-amine |

TABLE 1-continued

| Compound No. | Structure | Name |
|---|---|---|
| 43 | 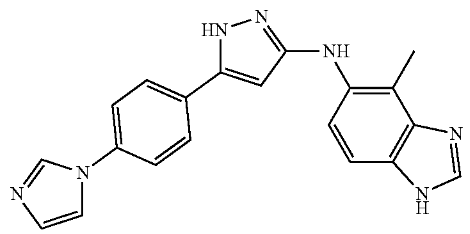 [SMILES: Cc1c(Nc2cc(-c3ccc(-n4ccnc4)cc3)[nH]n2)ccc2[nH]cnc12] | N-(5-(4-(1H-imidazol-1-yl)phenyl)-1H-pyrazol-3-yl)-4-methyl-1H-benzo[d]imidazol-5-amine |

Preferably, the compound of the present disclosure is chosen in Table 2 below.

TABLE 2

| Compound No. | Name |
|---|---|
| 2 | N-(5-(4-methoxyphenyl)-1H-pyrazol-3-yl)-1H-mdazol-5-amine |
| 6 | 6-((5-(4-hydroxyphenyl)-1H-pyrazol-3-yl)amino)-3,4-dihydroquinolin-2(1H)-one |
| 7 | 6-((5-(4-(1H-pyrazol-1-yl)phenyl)-1H-pyrazol-3-yl)ammo)-3,4-dihydroquinolin-2(1H)-one |
| 8 | 5-((5-(3-fluoro-4-hydroxyphenyl)-1H-pyrazol-3-yl)amino)indolin-2-one |
| 9 | 6-((5-(4-(1H-imidazol-1-yl)phenyl)-1H-pyrazol-3-yl)amino)-3,4-dihydroquinolin-2(1H)-one |
| 10 | N-(5-(4-(1H-pyrazol-1-yl)phenyl)-1H-pyrazol-3-yl)-1H-indazol-5-amine |
| 11 | 4-(3-((1H-indazol-5-yl)amino)-1H-pyrazol-5-yl)phenol |
| 12 | 4-(3-((1H-indazol-5-yl)amino)-1H-pyrazol-5-yl)-2-fluorophenol |
| 13 | 7-((5-(4-(1H-pyrazol-1-yl)phenyl)-1H-pyrazol-3-yl)amino)-2H-benzo[b][1,4]oxazin-3(4H)-one |
| 14 | 7-((5-(4-hydroxyphenyl)-1H-pyrazol-3-yl)amino)-2H-benzo[b][1,4]oxazin-3(4H)-one |
| 15 | 5-((5-(4-(1H-pyrazol-1-yl)phenyl)-1H-pyrazol-3-yl)amino)benzo[d]oxazol-2(3H)-one |
| 16 | N-(5-(4-fluorophenyl)-1H-pyrazol-3-yl)-1H-benzo[d]imidazol-6-amine |
| 17 | 6-((5-(4-(1H-pyrazol-1-yl)phenyl)-1H-pyrazol-3-yl)amino)-4-methylquinolin-2(1H)-one |
| 18 | N-(5-(4-(1H-pyrazol-1-yl)phenyl)-1H-pyrazol-3-yl)-2-methyl-1H-benzo[d]imidazol-5-amine |
| 19 | 5-((5-(4-(1H-pyrazol-1-yl)phenyl)-1H-pyrazol-3-yl)amino)-1,3-dihydro-2H-benzo[d]imidazole-2-thione |
| 20 | 6-((5-(4-(1H-pyrazol-1-yl)phenyl)-1H-pyrazol-3-yl)amino)benzo[d]thiazol-2(3H)-one |

In yet another embodiment, there is provided a pharmaceutical composition comprising a therapeutically effective amount of a compound of Chemical Formula 1 or a pharmaceutically acceptable salt thereof, and a pharmaceutically acceptable carrier.

In yet another embodiment, there is provided a pharmaceutical composition comprising a therapeutically effective amount of a compound of Chemical Formula 1 or a pharmaceutically acceptable salt thereof, a pharmaceutically acceptable carrier, and a therapeutically effective amount of an active pharmaceutical ingredient, which is not the compound of the present disclosure, selected from the group consisting of cytostatic drugs, angiogenesis inhibitors, kinase inhibitors, cytokine blockers and inhibitors of cell adhesion molecule inhibitors.

In another embodiment, there is provided a method for treating a disease or condition comprising administering to a subject in need thereof a therapeutically effective amount of a compound of Chemical Formula 1 or pharmaceutically acceptable salt thereof, wherein the disease or condition is selected from the group consisting of cancers, neoplasia, or tumors including colorectal cancer, breast cancer, brain tumor, gastric cancer, liver cancer, ovarian cancer, lung cancer, gastrointestinal cancer, leukemia, or melanoma. In another embodiment, the subject is a human. In another embodiment, the disease or condition is colorectal cancer.

That is, there is provided a medical use of Chemical Formula 1 or pharmaceutically acceptable salt thereof, wherein Chemical Formula 1 or pharmaceutically acceptable salt thereof is used as an effective agent. In one embodiment, the medical-use is for treatment or prevention of the disease or condition descried above.

Medical Uses and Methods of Treatment of the Compounds According to the Present Disclosure The present disclosure further provides methods for treating a disease or condition in a subject having or susceptible to having such a disease or condition, by administering to the subject a therapeutically-effective amount of one or more compounds as described above. In one embodiment, the treatment is preventative treatment. In another embodiment, the treatment is palliative treatment. In another embodiment, the treatment is restorative treatment.

1. Diseases or Conditions

The compound of the present disclosure for inhibiting TNIK activity is useful for treatment or prevention of various conditions (for example, anti-tumor). The compound can be used for inhibiting or hindering TNIK activity, and for treating a tumor or cancer, or for preventing aggravation of such disease. Thus, the present disclosure provides a method for inhibiting or hindering TNIK activity in a cell, wherein the cell is contacted with an effective amount of a compound of the present disclosure. In one embodiment, such cell is present in a subject (for example, cancer patients). In another embodiment, there is provided a medical use for treating cancer or preventing proliferation of tumor in a subject, using the compound according to the present disclosure. The method of the present disclosure comprises administering to a subject in need of treatment or prevention a pharmaceutical composition containing a therapeutically or prophylactically effective amount of TNIK inhibitor.

In one embodiment, there is provided a method for inhibiting or blocking TNIK activity in a tumor or cancer cell. For example, the present disclosure is used for inhibiting TNIK activity in a cell such as colorectal cancer cell, breast cancer cell, brain tumor cell, gastric cancer cell, liver cancer cell, ovarian cancer cell, lung cancer cell, gastrointestinal cancer cell, leukemia cell, or melanoma cell. In this method, the present disclosure provides a method for inhibiting the growth or proliferation of cells, particularly tumor or cancer cells, in a subject. In this method, tumor cells are present in vivo. The compound of the present disclosure can be administered to the subject as a form of the pharmaceutical composition described herein.

In another embodiment, there is provided a method for treating or preventing a cancer or tumor in a subject. The cancer includes, but is not limited to, colorectal cancer, breast cancer, brain tumor, gastric cancer, liver cancer, ovarian cancer, lung cancer, gastrointestinal cancer, leukemia, or melanoma. The method comprises administering to a subject in need of treatment an enough amount of the compound, that is, a therapeutically amount of the compound of the present disclosure.

2. Subjects

Suitable subjects to be treated according to the present disclosure include mammalian subjects. Mammals according to the present disclosure include, but are not limited to, human, canine, feline, bovine, caprine, equine, ovine, porcine, rodents, lagomorphs, primates, and the like, and encompass mammals in utero. Subjects may be of either gender and at any stage of development.

In one embodiment, the suitable subject to be treated according to the present disclosure is human.

3. Administration and Dosing

The compounds of the present disclosure are generally administered in a therapeutically effective amount.

The compounds of the present disclosure can be administered by any suitable route in the form of a pharmaceutical composition adapted to such a route, and in a dose effective for the treatment intended. An effective dosage is typically in the range of about 0.001 to about 100 mg per kg body weight per day, preferably about 0.01 to about 50 mg/kg/day, in single or divided doses. Depending on age, species and disease or condition being treated, dosage levels below the lower limit of this range may be suitable. In other cases, still larger doses may be used without harmful side effects. Larger doses may also be divided into several smaller doses, for administration throughout the day. Methods for determining suitable doses are well known in the art to which the present disclosure pertains. For example, Remington: The Science and Practice of Pharmacy, Mack Publishing Co., 20th ed., 2000 can be used.

Pharmaceutical Compostions, Dosage Forms and Administration Routes

For the treatment of the diseases or conditions referred to above, the compounds described herein or pharmaceutically acceptable salts thereof can be administered as follows:

Oral Administration

The compounds of the present disclosure may be administered orally, including by swallowing, so that the compound enters the gastrointestinal tract, or absorbed into the blood stream directly from the mouth (e.g., buccal or sublingual administration).

Suitable compositions for oral administration include solid, liquid, gel or powder formulations, and have a dosage form such as tablet, lozenge, capsule, granule or powder.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include, but are not limited to, lactose, starch, sodium starch glycolate, crospovidone, croscarmellose sodium, maltodextrin, or mixtures thereof.

Suitable lubricants, for use in a tablet, may be present in amounts from about 0.1% to about 5% by weight, and include, but are not limited to, talc, silicon dioxide, stearic acid, calcium, zinc or magnesium stearate, sodium stearyl fumarate and the like.

Suitable binders, for use in a tablet, include, but are not limited to, gelatin, polyethylene glycol, sugars, gums, starch, polyvinyl pyrrolidone, hydroxypropyl cellulose, hydroxypropylmethyl cellulose and the like. Suitable diluents, for use in a tablet, include, but are not limited to, mannitol, xylitol, lactose, dextrose, sucrose, sorbitol, microcrystalline cellulose and starch.

Suitable solubilizers, for use in a tablet, may be present in amounts from about 0.1% to about 3% by weight, and include, but are not limited to, polysorbates, sodium lauryl sulfate, sodium dodecyl sulfate, propylene carbonate, diethyleneglycol monoethyl ether, dimethyl isosorbide, polyethylene glycol (natural or hydrogenated) castor oil, HCOR™ (Nikkol), oleyl ester, Gelucire™, caprylic/caprylic acid mono/diglyceride, sorbitan fatty acid esters, and Solutol HS™.

Parenteral Administration

Compounds of the present disclosure may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release.

Most parenteral formulations are aqueous solutions containing excipients, including salts, buffering agents and isotonic agents.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Topical Administration

Compounds of the present disclosure may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical administration can also be performed by electroporation, iontophoresis, phonophoresis and the like.

Compositions for topical administration may be formulated as immediate or modified release, including delayed or sustained release.

References for Preparing Pharmaceutical Compositions

Methods for preparing pharmaceutical compositions for treating or preventing a disease or condition are well known in the art to which the present disclosure pertains. For example, based on *Handbook of Pharmaceutical Excipients* ($7^{th}$ ed.), *Remington: The Science and Practice of Pharmacy* ($20^{th}$ ed.), *Encyclopedia of Pharmaceutical Technology* ($3^{rd}$ ed.), or *Sustained and Controlled Release Drug Delivery Systems* (1978), pharmaceutically acceptable excipients, carriers, additives and so on can be selected and then mixed with the compounds of the present disclosure for making the pharmaceutical compositions.

Combinations and Combination Therapy

The compounds of the present disclosure can be used, alone or in combination with other pharmaceutically active compounds, to treat conditions such as those previously described above. The compound(s) of the present invention and other pharmaceutically active compound(s) can be administered simultaneously (either in the same dosage form or in separate dosage forms) or sequentially. Accordingly, in one embodiment, the present disclosure comprises methods for treating a condition by administering to the subject a therapeutically-effective amount of one or more compounds of the present disclosure and one or more additional pharmaceutically active compounds.

In another embodiment, there is provided a pharmaceutical composition comprising one or more compounds of the present disclosure, one or more additional pharmaceutically active compounds, and a pharmaceutically acceptable carrier In another embodiment, the one or more additional pharmaceutically active compounds is an anti-cancer drug. For example, the anti-cancer drug is EGFR kinase inhibitors, MEK inhibitors, VEGFR inhibitors, anti-VEGFR2 antibodies, KDR antibodies, AKT inhibitors, PDK-1 inhibitors, PI3K inhibitors, c-kit/Kdr tyrosine kinase inhibitors, Bcr-Abl tyrosine kinase inhibitors, VEGFR2 inhibitors, PDGFR-beta inhibitors, KIT inhibitors, Flt3 tyrosine kinase inhibitors, PDGF receptor family inhibitors, Flt3 tyrosine kinase inhibitors, RET tyrosine kinase receptor family inhibitor, VEGF-3 receptor antagonists, Raf protein kinase family inhibitor, angiogenesis inhibitors, Erb2 inhibitors, mTOR inhibitors, IGF-1R antibodies, NFkB inhibitors, proteasome inhibitors, chemotherapy agents, or glucose reduction agents.

In one embodiment, an active agent used in the combination medicine and/or combination therapy with the compound(s) of the present disclosure is an anti-cancer drug. That is, the compound(s) of the present invention may be administered concurrently or sequentially to a subject who is taking one or more anti-cancer drug. Such anti-cancer drug includes, but is not limited to, alkylating agents such as nitrogen mustard, chlorambucil, cytoxan, ifosfamide, melphalan, thiptepa and busulfan; antimetabolites such as methotrexate, 5-fluorouracil, cytoxine arabinoside (ara-C), 5-azacitidine, 6-mercaptopurine, 6-thioguanine, and fludarabine phosphate; antitumor antibiotics such as doxorubicin, adriamycin, daunorubicin, dactinomycin, bleomycin, mitomycin C, plicamycin, idarubicin, and mitoxantrone; vinca alkaloids and epipodophyllotoxins such as vincristine, vinblastine, vindesine, etoposide, and teniposide; nitrosoureas such as carmustine, lomustine, semustine and streptozotocin; synthetic agents such as dacrabazine, hexamethyl melamine, hydroxyurea, mitotane procabazine, cisplatin, cisplatinum and carboplatin; corticosteroids (cortisone acetate, hydrocortisone, prednisone, prednisolone, methyl prednisolone and dexamethasone), estrogens (diethylstilbestrol, estradiol, esterified estrogens, conjugated estrogens, chlorotrianisene), progesterones (medroxyprogesterone acetate, hydroxy progesterone caproate, megestrol acetate), anti-estrogens (tamoxifen), aromastase inhibitors (aminoglutethimide), androgens (testosterone propionate), methyl testosterone, fluoxymesterone, testolactone), anti-androgens (flutamide), LHRH analogues (leuprolide acetate), and endocrines for prostate cancer (ketoconazole).

In one embodiment, an active agent used in the combination medicine and/or combination therapy with the compound(s) of the present disclosure is a drug for colorectal cancer. In another embodiment, the drug for colorectal cancer is based on regimens FOLFOX or FOLFIRI including 5-FU, leucovorin, oxaliplatin, irinotecan or their combinations. In a conventional standard method of treatment, the combination therapy is used together with cetuximab and/or bevacizumab. When the compound of the present disclosure is used with other anti-colon drugs, the compound of the present disclosure may be locally administered by injection to treat non-invasive colon cancer.

Therapeutically effective dosages vary when the drugs are used in treatment combinations. Combination treatment further includes periodic treatments that start and stop at various times to assist with the clinical management of the patient. In any case, the multiple therapeutic agents (one of which is a TNIK inhibitor as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from, a few minutes to several hours, depending upon the properties of each pharmaceutical agent, such as potency, solubility, bioavailability, plasma half-life and kinetic profile of the pharmaceutical agent. Circadian variation of the target molecule concentration is optionally used to determine the optimal dose interval.

Advantageous Effects of Invention

The present disclosure provides a compound having various pharmacological effects by inhibiting TNIK activity, a pharmaceutical composition having the compound as an effective agent, a medical use, particularly for treating cancers, of the compound, and a method of treatment or prevention comprising administering the compound to a subject in need of such treatment or prevention. The compounds of the present disclosure and pharmaceutically acceptable salts thereof have good safety and high selectivity for TNIK, and thus exhibit superior property as a drug.

MODE FOR THE INVENTION

Hereinafter, the present disclosure is described in considerable detail with examples to help those skilled in the art understand the present disclosure. However, the following examples are offered by way of illustration and are not intended to limit the scope of the invention. It is apparent that various changes may be made without departing from the spirit and scope of the invention or sacrificing all of its material advantages.

Preparation of Compounds of the Present Disclosure

Reagents and solvents used below were purchased from Aldrich Chemical Co. (Milwaukee, Wis., USA). $^1$H-NMR spectra were evaluated with Bruker Avance 300 MHz, Bruker Avance III HD 300 MHz, Bruker Avance 500 MHz NMR spectrometer and so on.

Below, the illustrating synthetic examples of some compounds of the present disclosure are described, and other compounds can be prepared by the similar method to one described below with different starting or reacting materials.

Synthesis Example 1: Preparation of N-(5-(4-methoxyphenyl)-1H-pyrazol-3-yl)-1H-indol-5-amine Step 1. 1-(4-methoxyphenyl)-3,3-bis(methylthio)prop-2-en-1-one

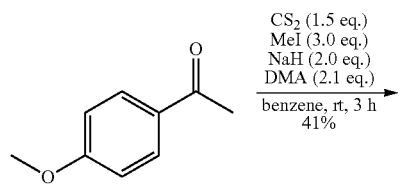

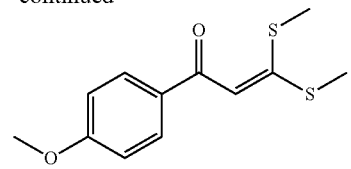

4-methoxyacetophenone (10.0 g, 66.6 mmol) and benzene (220 mL) were mixed at ambient temperature in a 500 mL round flask. After cooled using an ice bath, NaH (5.32 g, 133.0 mmol, 2.0 eq.) was added slowly and stirred for 5 minutes. Carbon disulfide (6.0 mL, 99.9 mmol, 1.5 eq.) was added slowly and stirred at ambient temperature for 5 minutes, and then iodomethane (12.4 mL, 199.8 mmol, 3.0 eq.) was added slowly and stirred at ambient temperature for 5 minutes. After that, N, N-dimethylacetamide (13 mL, 139.9 mmol, 2.1 eq.) was added slowly and stirred at ambient temperature for 3 hours. After the reaction ended, $H_2O$ was added for quenching, and the reactant was extracted with EtOAc. The organic solvent layer wad dried over $MgSO_4$ and concentrated in vacuo. After that, it was filtered with $Et_2O$ to provide the compound as a yellow solid (6.97 g) (yield: 41%).

Step 2. (Z)-3-((1H-indol-5-yl)amino)-1-(4-methoxyphenyl)-3-(methylthio)prop-2-en-1-one

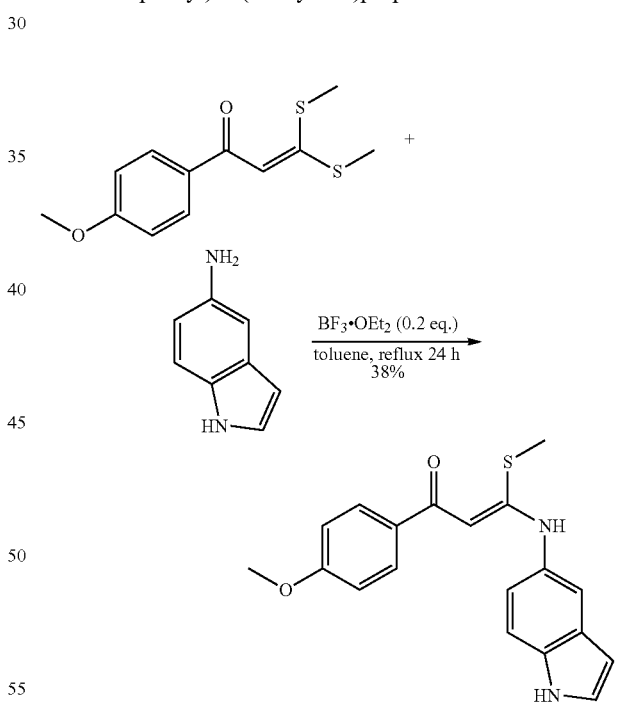

1-(4-methoxyphenyl)-3,3-bis(methylthio)prop-2-en-1-one (127 mg, 0.5 mmol) prepared in Step 1 and toluene (5 mL) were added in a vial for microwave reaction, and then stirred. Then $BF_3 \cdot OEt_2$ (13 μL, 0.1 mmol, 0.2 eq.) was added, and 5-aminoindole (100 mg, 0.75 mmol, 1.5 eq.) was added. After that, the reaction mixture was reacted under reflux for 24 hours. After the reaction ended, the solvent was removed with a rotavapor and the remaining reactant was filtered with MeOH to provide the compound as a brown solid (65 g) (yield: 38%).

Step 3. N-(5-(4-methoxyphenyl)-1H-pyrazol-3-yl)-1H-indol-5-amine

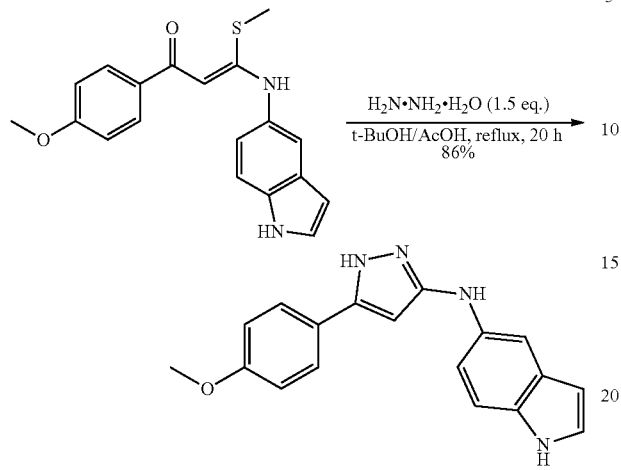

(Z)-3-((1H-indol-5-yl)amino)-1-(4-methoxyphenyl)-3-(methylthio)prop-2-en-1-one (54 mg, 0.16 mmol), t-BuOH (3 mL) prepared in Step 2 and AcOH (10 μL) were added in a 50 mL round flask and stirred. Hydrazine hydrate (10 μL, 0.24 mmol, 1.5 eq.) was added and reacted under reflux for 20 hours. After the reaction ended, the solvent was removed with a rotavapor and extracted with $H_2O$ (50 ml) and EtOAc (50 mL×3), and then the organic solvent layer was dried over $MgSO_4$ and concentrated in vacuo. After that, the reactant was separated using silica gel column chromatography (EtOAc:Hex) to provide the compound as a yellow solid (42 mg) (yield: 86%).

$^1$H-NMR (500 MHz, DMSO-d6) δ 10.71 (s, —NH), 8.21 (s, 1H), 7.66 (d, 2H, J=8.1 Hz), 7.62 (s, 1H), 7.32 (d, 1H, J=8.5 Hz), 7.09 (s, 1H), 7.02 (d, 2H, 8.2 Hz), 6.85 (d, 1H, J=8.6 Hz), 3.80 (s, 3H).

Synthesis Example 2: Preparation of 6-((5-(4-(benzyloxy)phenyl)-1H-pyrazol-3-yl)amino)-3,4-dihydroquinolin-2(1H)-one Step 1. 7-nitro-1,4-dihydroisoquinolin-3(2H)-one

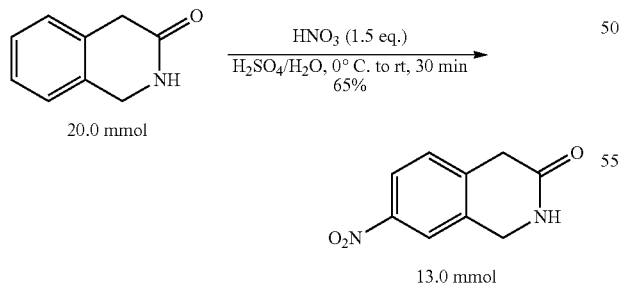

3,4-Dihydro-2-(1H)-quinolinone (2.94 g, 20.0 mmol) and $H_2SO_4$ (60 mL) were added in a 250 mL round flask and stirred at ambient temperature. After cooled using an ice bath, $H_2O$ (30 mL) was added and $HNO_3$ (2.1 mL, 30.0 mmol, 1.5 eq.) was added dropwise, and then the reaction mixture was stirred at ambient temperature for 30 minutes. After the reaction ended, ice water was added, and the reactant was extracted with $H_2O$ (50 ml) and EtOAc (50 mL×3). The organic solvent layer was dried over $MgSO_4$ and concentrated in vacuo. After that, the reactant was filtered with EtOAc to provide the compound (2.5 g) (yield: 65%).

Step 2. 7-amino-1,4-dihydroisoquinolin-3(2H)-one

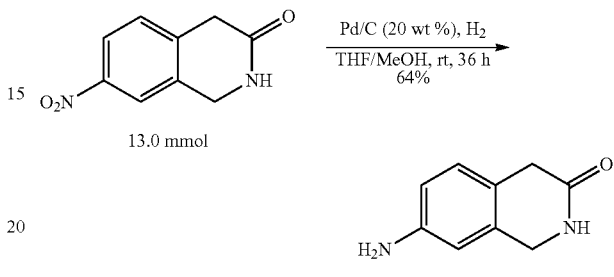

7-nitro-1,4-dihydroisoquinolin-3(2H)-one (2.5 g, 13.0 mmol, 1.0 eq.) and THF/MeOH (50/50 mL) were stirred at ambient temperature in a 250 mL round flask. Pd/C (500 mg, 20 wt %) was added and stirred at ambient temperature for 24 hours. Pd/C (250 mg, 10 wt %) was further added and stirred at ambient temperature for 12 hours. After the reaction ended, Pd/C was removed using a celite filter and the solvents were removed with a rotavapor. The reactant then was separated using silica gel column chromatography (EtOAc:Hex) to provide the compound (1.35 g) (yield: 64%).

Step 3. 6-((5-(4-(benzyloxy)phenyl)-1H-pyrazol-3-yl)amino)-3,4-dihydroquinolin-2(1H)-one

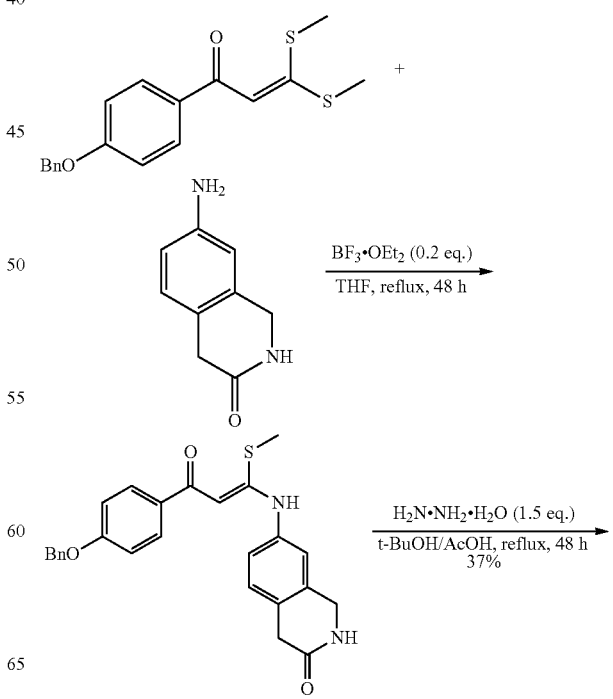

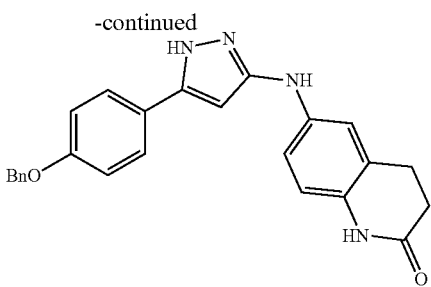

1-(4-(benzyloxy)phenyl)-3,3-bis(methylthio)prop-2-en-1-one (660 mg, 2.0 mmol) and Toluene (10 mL) were stirred in a MW vial. To the vial $BF_3 \cdot OEt_2$ (50 μL, 0.4 mmol, 0.2 eq.) and 7-amino-1,4-dihydroisoquinolin-3(2H)-one (487 mg, 3.0 mmol, 1.5 eq.) prepared in Step 2 were added and reacted at 120° C. for 24 hours. After the reaction ended, the solvent was removed using a rotavapor and the reactant was extracted with $H_2O$ (50 ml) and EtOAc (50 mL×3). The organic solvent layer was dried over $MgSO_4$ and concentrated in vacuo. t-BuOH (10 mL), AcOH (75 μL) and Hydrazine hydrate (150 μL, 3.0 mmol, 1.5 eq.) were added and reacted under reflux for 24 hours. After the reaction ended, the solvent was removed using a rotavapor and extracted with $H_2O$ (50 ml) and EtOAc (50 mL×3). The organic solvent layer was dried over $MgSO_4$ and concentrated in vacuo. After that, silica gel column chromatography (EtOAc:Hex) separated the compound (2 steps, 307 mg) (yield: 37%).

$^1$H NMR (300 MHz, Chloroform-d) δ 7.96 (d, J=8.9 Hz, 2H), 7.85 (s, 1H), 7.50-7.32 (m, 5H), 7.13 (d, J=8.3 Hz, 2H), 7.05 (d, J=8.9 Hz, 2H), 6.80 (d, J=8.0 Hz, 1H), 6.15 (s, 1H), 5.15 (s, 2H), 3.01 (t, J=7.5 Hz, 2H), 2.73-2.61 (m, 2H), 2.52 (s, 3H).

Synthesis Example 3: Preparation of 6-((5-(4-hydroxyphenyl)-1H-pyrazol-3-yl)amino)-3,4-dihydroquinolin-2(1H)-one

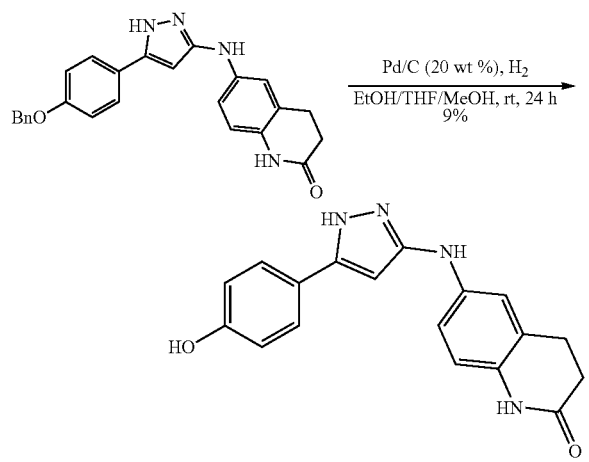

6-((5-(4-(benzyloxy)phenyl)-1H-pyrazol-3-yl)amino)-3,4-dihydroquinolin-2(1H)-one (300 mg, 0.73 mmol) and EtOAc/THF/MeOH (20/20/20 mL) were stirred at ambient temperature in a 100 mL round flask. Pd/C (60 mg, 20 wt %) was added and stirred at ambient temperature for 24 hours. After the reaction ended, Pd/C was removed using a celite pad and the solvents were removed using a rotavapor. After that, silica gel column chromatography (DCM:MeOH) separated the compound (21 mg) (yield: 9%).

$^1$H NMR (300 MHz, DMSO-$d_6$) δ 12.12 (s, 1H), 9.80 (s, 1H), 9.65 (s, 1H), 8.18 (s, 1H), 7.51 (d, J=8.6 Hz, 2H), 7.21 (s, 1H), 7.13-7.04 (m, 1H), 6.80 (d, J=8.6 Hz, 2H), 6.69 (d, J=8.5 Hz, 1H), 6.02 (s, 1H), 2.80 (t, J=7.5 Hz, 2H), 2.39 (t, J=7.4 Hz, 2H).

Synthesis Example 4: Preparation of N-(5-(4-fluorophenyl)-1H-pyrazol-3-yl)-1H-benzo[d]imidazol-6-amine XPhos Pd G1 (5 mol %, 0.0113 mmol, 5.4 mg), XPhos (7 mol %, 0.0158 mmol, 11.6 mg), NaOtBu (2.1 eq, 0.475 mmol, 45 mg), pyrazole amine (1.0 eq, 0.226 mol, 40 mg), 6-Bromobenzimidazole (1.2 eq, 0.271 mmol, 53 mg), and degassed t-BuOH (4 mL) was added in a microwave vial. Microwave irradiation was performed at 150° C. for 1 hour. After cooled to room temperature, the reacting mixture was washed with cold ether and filtered to provide the compound (20 mg) (yield: 30%).

$^1$H NMR (300 MHz, $CDCl_3$) δ 7.98 (s, 1H), 7.76 (d, J=1.8 Hz, 1H), 7.57-7.50 (m, 2H), 7.46 (s, 1H), 7.36 (dd, J=8.6, 1.8 Hz, 1H), 7.06 (t, J=8.7 Hz, 2H), 5.87 (s, 1H).

The compounds of the present disclosure were synthesized using the method described above by adjusting starting materials and/or intermediates. Results of $^1$H NMR tests are written in Table 3 below.

TABLE 3

| Compound No. | 1H NMR |
|---|---|
| 1 | $^1$H-NMR (500 MHz, DMSO-d6) δ 10.71 (s, —NH), 8.21 (s, 1H), 7.66 (d, 2H, J = 8.1 Hz), 7.62 (s, 1H), 7.32 (d, 1H, J = 8.5 Hz), 7.09 (s, 1H), 7.02 (d, 2H, 8.2 Hz), 6.85 (d, 1H, J = 8.6 Hz), 3.80 (s, 3H). |

TABLE 3-continued

| Compound No. | 1H NMR |
|---|---|
| 2 | $^1$H-NMR (500 MHz, CDCl$_3$) δ 13.31 (s, —NH), 8.25 (s, 1H), 7.94 (d, 2H, J = 8.4 Hz), 7.61 (s, 1H), 7.41 (d, 1H, J = 8.5 Hz), 7.16 (d, 1H, J = 8.7 Hz), 6.98 (d, 2H, J = 6.98 Hz), 6.59 (s, 1H), 5.86 (s, 1H), 3.90 (s, 3H), 2.44 (s, 3H). |
| 3 | $^1$H-NMR (300 MHz, DMSO-d6) δ 12.14 (s, —NH), 10.35 (s, —NH), 10.19 (s, —NH), 8.12 (s, 1H), 7.64 (d, 2H, J = 8.3 Hz), 7.23 (s, —NH), 7.00 (d, 2H, J = 8.4 Hz), 6.80-6.72 (m, 2H), 6.06 (s, 1H), 3.43 (s, 2H), 3.79 (s, 3H). |
| 4 | $^1$H-NMR (300 MHz, DMSO-d6) δ 12.16 (s, 1H), 10.07 (s, 1H), 8.13 (s, 1H), 7.63 (d, 2H, J = 8.8 Hz), 7.30 (s, 1H), 7.12 (s, 1H), 6.99 (d, 2H, J = 8.9 Hz), ), 6.65 (d, 1H, J = 8.3 Hz), 6.07 (s, 1H), 3.78 (s, 3H). |
| 5 | $^1$H NMR (300 MHz, Chloroform-d) δ 7.96 (d, J = 8.9 Hz, 2H), 7.85 (s, 1H), 7.50-7.32 (m, 5H), 7.13 (d, J = 8.3 Hz, 2H), 7.05 (d, J = 8.9 Hz, 2H), 6.80 (d, J = 8.0 Hz, 1H), 6.15 (s, 1H), 5.15 (s, 2H), 3.01 (t, J = 7.5 Hz, 2H), 2.73-2.61 (m, 2H), 2.52 (s, 3H). |
| 6 | $^1$H NMR (300 MHz, DMSO-d$_6$) δ 12.12 (s, 1H), 9.80 (s, 1H), 9.65 (s, 1H), 8.18 (s, 1H), 7.51 (d, J = 8.6 Hz, 2H), 7.21 (s, 1H), 7.13-7.04 (m, 1H), 6.80 (d, J = 8.6 Hz, 2H), 6.69 (d, J = 8.5 Hz, 1H), 6.02 (s, 1H), 2.80 (t, J = 7.5 Hz, 2H), 2.39 (t, J = 7.4 Hz, 2H). |
| 7 | $^1$H NMR (300 MHz, DMSO-d$_6$) δ 12.43 (s, 1H), 9.82 (s, 1H), 8.55 (d, J = 2.6, 1H), 8.26 (s, 1H), 7.91 (d, J = 8.6, 2H), 7.84 (d, J = 8.6, 2H), 7.77 (d, J = 1.5, 1H), 7.23 (s, 1H), 7.12 (s, 1H), 6.71 (d, J = 8.5 Hz, 1H), 6.57 (t, J = 2.1, 1H), 6.25 (s, 1H), 2.81 (t, J = 7.5, 2H), 2.40 (t, J = 7.5, 2H). |
| 8 | $^1$H-NMR (300 MHz, DMSO-d6) δ 10.16 (s, 1H), 7.58 (dd, J = 12.4, 2.1, 1H), 7.40 (d, J = 9.5, 1H), 7.23 (s, 1H), 7.09 (d, J = 8.3 Hz, 1H), 7.01 (t, J = 8.8, 1H), 6.70 (d, J = 8.3 Hz, 2H), 6.20 (s, 1H), 3.43 (s, 2H). |
| 9 | $^1$H NMR (300 MHz, DMSO-d$_6$) δ 9.82 (s, 1H), 8.32 (s, 1H), 8.26 (s, 1H), 7.87-7.81 (m, 3H), 7.73 (d, J = 8.7, 1H), 7.18 (s, 1H), 7.13 (s, 1H), 7.09 (d, J = 8.5 Hz, 1H), 6.71 (d, J = 8.5, 1H), 6.28 (s, 1H), 2.81 (t, J = 7.5, 2H), 2.54 (s, 3H), 2.40 (d, J = 7.5, 2H). |
| 10 | $^1$H NMR (300 MHz, DMSO-d 6) δ 12.72 (s, 1H), 12.43 (s, 1H), 8.56 (d, J = 2.5 Hz, 1H), 8.34 (s, 1H), 7.95-7.83 (m, 5H), 7.77 (d, J = 1.7 Hz, 1H), 7.39 (d, J = 8.9 Hz, 1H), 7.24 (d, J = 9.2 Hz, 1H), 6.57 (t, J = 2.1 Hz, 1H), 6.31 (s, 1H). |
| 11 | $^1$H NMR (300 MHz, DMSO-d$_6$) δ 12.71 (s, 1H), 12.12 (s, 1H), 9.63 (s, 1H), 8.27 (s, 1H), 7.87 (d, J = 7.1 Hz, 2H), 7.53 (d, J = 8.3 Hz, 2H), 7.37 (d, J = 8.9 Hz, 1H), 7.22 (d, J = 9.0 Hz, 1H), 6.82 (d, J = 8.4 Hz, 2H), 6.07 (s, 1H). |
| 12 | $^1$H NMR (300 MHz, DMSO-d$_6$) δ 12.71 (s, 1H), 12.20 (s, 1H), 10.07 (s, 1H), 8.28 (s, 1H), 7.87 (s, 1H), 7.53 (dd, J = 12.5, 2.0 Hz, 1H), 7.37 (d, J = 8.6 Hz, 2H), 7.22 (d, J = 9.1 Hz, 1H), 6.99 (t, J = 8.8 Hz, 1H), 6.16 (s, 1H), 5.75 (s, 1H). |
| 13 | (300 MHz, DMSO-d$_6$) δ 12.47 (s, 1H), 10.43 (s, 1H), 8.56 (d, J = 2.5 Hz, 1H), 8.42 (s, 1H), 7.92 (d, J = 8.5 Hz, 2H), 7.84 (d, J = 8.5 Hz, 2H), 7.77 (d, J = 1.7 Hz, 1H), 7.14 (s, 1H), 6.90 (d, J = 6.9 Hz, 1H), 6.74 (d, J = 8.4 Hz, 1H), 6.57 (t, J = 2.1 Hz, 1H), 6.24 (s, 1H), 4.49 (s, 2H). |
| 14 | (300 MHz, DMSO-d$_6$) δ 12.17 (s, 1H), 10.41 (s, 1H), 9.66 (s, 1H), 8.33 (s, 1H), 7.52 (d, J = 8.4 Hz, 2H), 7.14 (s, 1H), 6.88 (d, J = 8.7 Hz, 1H), 6.81 (d, J = 8.5 Hz, 2H), 6.72 (d, J = 8.5 Hz, 1H), 6.01 (s, 1H), 4.49 (s, 2H). |
| 15 | (300 MHz, DMSO-d$_6$) δ 12.49 (s, 1H), 11.32 (s, 1H), 8.56 (d, J = 2.4 Hz, 1H), 8.53 (s, 1H), 7.93 (d, J = 8.5 Hz, 2H), 7.84 (d, J = 8.6 Hz, 2H), 7.77 (d, J = 1.7 Hz, 1H), 7.41 (s, 1H), 7.09 (d, J = 8.7 Hz, 1H), 6.92 (d, J = 8.8 Hz, 1H), 6.57 (t, J = 2.1 Hz, 1H), 6.25 (s, 1H). |
| 16 | $^1$H NMR (300 MHz, CDCl—$_3$) δ 7.98 (s, 1H), 7.76 (d, J = 1.8 Hz, 1H), 7.57-7.50 (m, 2H), 7.46 (d, J = 8.6, 1.8 Hz, 1H), 7.36 (dd, J = 8.6, 1.8 Hz, 1H), 7.06 (t, J = 8.7 Hz, 2H), 5.87 (s, 1H). |
| 17 | (300 MHz, DMSO-d$_6$) δ 11.40 (s, 1H), 8.62-8.46 (m, 2H), 7.88 (q, J = 8.7 Hz, 5H), 7.77 (d, J = 1.7 Hz, 1H), 7.45 (d, J = 8.8 Hz, 1H), 7.22 (d, J = 8.8 Hz, 1H), 6.57 (t, J = 2.1 Hz, 1H), 6.34 (d, J = 22.6 Hz, 2H), 2.40 (d, J = 1.2 Hz, 4H). |
| 18 | (300 MHz, DMSO-d$_6$) δ 11.80 (s, 1H), 8.57 (d, J = 2.6 Hz, 1H), 8.19 (s, 1H), 7.98-7.76 (m, 4H), 7.30 (d, J = 8.6 Hz, 1H), 6.58 (s, 1H), 6.27 (s, 1H), 2.43 (d, J = 4.0 Hz, 2H), 2.09 (s, 1H), 1.12 (s, 1H). |
| 19 | (300 MHz, DMSO-d$_6$) δ 12.24 (s, 2H), 12.08 (s, 1H), 8.55 (d, J = 2.6 Hz, 1H), 8.50 (s, 1H), 7.92 (d, J = 8.5 Hz, 2H), 7.84 (d, J = 8.6 Hz, 2H), 7.78 (d, J = 1.7 Hz, 1H), 7.51 (s, 1H), 6.99 (s, 2H), 6.58 (t, J = 2.2 Hz, 1H), 6.26 (s, 1H), 5.35 (s, 1H), 4.95 (s, 1H). |
| 20 | (300 MHz, DMSO-d$_6$) δ 12.49 (s, 1H), 8.57 (d, J = 2.6 Hz, 1H), 8.48 (s, 1H), 7.99-7.83 (m, 3H), 7.78 (d, J = 1.7 Hz, 1H), 7.66 (d, J = 1.5 Hz, 1H), 7.19 (s, 1H), 6.97 (d, J = 8.6 Hz, 2H), 6.58 (t, J = 2.1 Hz, 1H), 6.30 (s, 1H). |
| 21 | $^1$H NMR (300 MHz, DMSO-d$_6$) δ 10.26 (s, 1H), 8.70 (d, J = 2.6 Hz, 1H), 8.22 (d, J = 8.7 Hz, 2H), 8.05 (d, J = 8.7 Hz, 2H), 7.84 (d, J = 1.7 Hz, 1H), 7.11-6.99 (m, 2H), 6.95 (d, J = 8.3 Hz, 1H), 6.64 (s, 2H), 2.93 (t, J = 7.4 Hz, 2H), 2.70 (s, 3H), 2.46 (s, 2H). |

Evaluation of Compounds

1. Efficacy of Inhibiting TNIK Activity, In Vitro TNIK Kinase Assay Using qPCR

For most assays, kinase-tagged T7 phage strains were grown in parallel in 24-well blocks in an E. coli host derived from the BL21 strain. E. coli were grown to log-phase and infected with T7 phage from a frozen stock (multiplicity of infection=0.4) and incubated with shaking at 32° C. until (90-150 minutes). The lysates were centrifuged (6,000×g) and filtered (0.2 µm) to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 40× stocks in 100% DMSO and directly diluted into the assay. All reactions were performed in polypropylene 384-well plates in a final volume of 0.04 ml.

The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR.

Results are shown in Table 4 below.

TABLE 4

| Compound no. | Activity(%) at 1 µM |
| --- | --- |
| 1 | 16 |
| 2 | 21 |
| 3 | 7 |
| 4 | 8 |

As shown in Table 4 above, the compounds of the present disclosure were very effective in inhibiting TNIK activity.

2. Efficacy of Inhibiting TNIK Activity, In Vitro TNIK Kinase Assay Using ADP-Glo™ Kinase Assay System The inhibitory properties of compounds were evaluated with TNIK kinase enzyme system and luminescent ADP-Glo™ Kinase Assay from Promega Corporation according to the manufacturer's protocol. The tested compounds were incubated with TNIK kinases. Reactions were performed in 10 µl kinase buffer supplemented with reaction mixture containing 2 µl ATP, 2 µl MBP protein and 2 µl TNIK at 37° C. for 30 min. The exact reactions' conditions are provided in Table 5. After kinase reaction, 5 µl reaction mixtures were transferred to 384 well assay plate (Greiner, solid white low-binding plates). Next, 5 µl of ADP-Glo Reagent was added to each well and incubated at 37° C. for 30 min. After 45 min, 10 µl Kinase Detection Reagent was added to each well and luminescence signal was detected with the SpectraMax M5e Microplate Reader (Molecular Devices, Menlo Park, Calif.) after 30 min at 37° C. incubation. The $IC_{50}$ values were calculated using GraphPad Prism software (GraphPad Software Inc., La Jolla, Calif., USA) to determine kit performance. To the cut-off assay, the inhibitory activity of the compounds against TNIK kinase was expressed as the percentage of the kinase inhibitory activity for an indicated concentration of inhibitor. The IC s of the compounds against TNIK kinase values were calculated a log-concentration-response curve fitted with a four-parameter logistic equation and expressed dose-response curve for % of inhibitory activity versus log of the compound concentration.

The reactions' conditions to be used in vitro TNIK kinase inhibitory assay are shown in Table 5.

TABLE 5

| TNIK kinase(ng/ reaction) | MBP substrate(µg/ reaction) | ATP(µM) | Other reagents |
| --- | --- | --- | --- |
| 13 | 1 | 100 | Kinase buffer (40 mM Tris (pH 7.5), 20 mM MgCl2, 0.1 mg/ml BSA) |

Results of in vitro TNIK kinase assay (HTRF) are shown in Tables 6 and 7 below.

TABLE 6

| Compound No. | $IC_{50}$ (nM) |
| --- | --- |
| 2 | 94 |
| 6 | 62 |
| 7 | 1 |
| 8 | 1 |
| 9 | 1 |
| 10 | 55 |
| 11 | 29 |
| 12 | 45 |
| 13 | 7 |
| 18 | 96 |

TABLE 7

| Compound No. | Inhibition (%) at 1 µM |
| --- | --- |
| 2 | 99 |
| 3 | 79 |
| 6 | 96 |
| 8 | 88 |
| 9 | 98 |
| 10 | 99 |
| 11 | 94 |
| 12 | 93 |
| 13 | 90 |
| 14 | 97 |
| 18 | 99 |
| 19 | 97 |

3. Efficacy of Inhibiting Cancer Cells Using Colon Cancer Cell Lines

1) Cell Culture

The human colon cancer cell line SW480 (Catalog No. CCL-228) and SW620 (Catalog No. CCL-227) were obtained from the American Type Culture Collection (ATCC), and maintained in DMEM (Thermo Fisher Scientific Inc., Waltham, Mass., USA) supplemented with 10% fetal bovine serum (FBS) (Thermo Fisher Scientific Inc., Waltham, Mass.), 100 U/ml penicillin, and 100 g/ml streptomycin (Gibco, Gaithersburg, Md.). Cells were grown at 37° C. in 5% $CO_2$ for confluence.

2) Cell Viability Assay

Cell viability was measured using the Cell Counting Kit-8 (Dojindo Molecular Technologies). SW480 and SW620 cells ($2.5 \times 10^4$ cells/well) were seeded in 96-well plates and incubated for 24 h. After incubation, the cells were exposed to serially diluted compounds (0.1, 0.3, 1, 3, 10 and 30 M)

in 100 μl phenol free DMEM medium containing 0.1% FBS. After 48 h, CCK-8 reagent was added at 10 μl per well and incubated for 1 h at 37° C. Optical density was measured at 450 nm using a microplate reader (Bio-Rad Laboratories, Hercules, Calif.). The $IC_{50}$ values were calculated using GraphPad Prism software (GraphPad Software Inc., La Jolla, Calif., USA) to determine kit performance. Experiments were performed in triplicate.

Results of cell viability assay using SW620 cell are shown in Table 8 below.

TABLE 8

| Compound No. | $IC_{50}$ (μM) SW620 |
|---|---|
| 2 | 1.2 |
| 12 | 13 |
| 18 | 3.4 |

Results of cell viability assay using SW480 cell are shown in Table 9 below.

TABLE 9

| Compound No. | $IC_{50}$ (μM) SW480 |
|---|---|
| 2 | 4.5 |
| 18 | 21 |

All mentioned documents are incorporated by reference as if herein written. When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations.

The invention claimed is:

1. A compound of Chemical Formula 1:

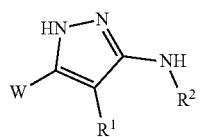

[Chemical Formula 1]

or a pharmaceutically acceptable salt thereof,
in the Chemical Formula 1
W is substituted phenyl, pyridyl, thiophene, thiazole, pyrrole, benzothiophene, or indole,
$R^1$ is H or F,
$R^2$ is 1H-indole, 1H-indazole, 1,3-dihydro-2H-benzo[d]imidazol-2-one, 3,4-dihydroquinolin-2(1H)-one, indolin-2-one, benzo[b][1,4]oxazin-3(4H)-one, benzo[d]oxazol-2(3H)-one, 2-methyl-1 H-benzo[d]imidazole, 4-methylquinolin-2(1 H)-one, 1,3-dihydro-2H-benzo[d]imidazole-2-thione, benzo[d]thiazol-2(3H)-one, 4-methyl-1H-indazol, 6-methyl-1H-indazol, 4-methyl-1H-benzo[d]imidazole, or 6-methyl-1H-benzo[d]imidazole, or 1H-benzo[d]im idazole.

2. The compound of claim 1, in the Chemical Formula 1, wherein W is a substituted phenyl.

3. The compound of claim 1, wherein the compound is
N-(5-(4-methoxyphenyl)-1H-pyrazol-3-yl)-1H-indol-5-amine,
N-(5-(4-methoxyphenyl)-1H-pyrazol-3-yl)-1H-indazol-5-amine,
5-((5-(4-methoxyphenyl)-1H-pyrazol-3-yl)amino)-1,3-dihydro-2H-benzo[d]imidazol-2-one,
N-(5-(4-methoxyphenyl)-1H-pyrazol-3-yl)-1H-indazol-6-amine,
6-((5-(4-(benzyloxy)phenyl)-1H-pyrazol-3-yl)amino)-3,4-dihydroquinolin-2(1H)-one,
6-((5-(4-hydroxyphenyl)-1H-pyrazol-3-yl)amino)-3,4-dihydroquinolin-2(1H)-one,
6-((5-(4-(1H-pyrazol-1-yl)phenyl)-1H-pyrazol-3-yl)amino)-3,4-dihydroquinolin-2(1H)-one,
5-((5-(3-fluoro-4-hydroxyphenyl)-1H-pyrazol-3-yl)amino)indolin-2-one,
6-((5-(4-(1H-imidazol-1-yl)phenyl)-1H-pyrazol-3-yl)amino)-3,4-dihydroquinolin-2(1H)-one,
N-(5-(4-(1H-pyrazol-1-yl)phenyl)-1H-pyrazol-3-yl)-1H-indazol-5-amine,
4-(3-((1H-indazol-5-yl)amino)-1H-pyrazol-5-yl)phenol,
4-(3-((1H-indazol-5-yl)amino)-1H-pyrazol-5-yl)-2-fluorophenol,
7-((5-(4-(1H-pyrazol-1-yl)phenyl)-1H-pyrazol-3-yl)amino)-2H-benzo[b][1,4]oxazin-3(4H)-one,
7-((5-(4-hydroxyphenyl)-1H-pyrazol-3-yl)amino)-2H-benzo[b][1,4]oxazin-3(4H)-one,
5-((5-(4-(1H-pyrazol-1-yl)phenyl)-1H-pyrazol-3-yl)amino)benzo[d]oxazol-2(3H)-one,
N-(5-(4-fluorophenyl)-1H-pyrazol-3-yl)-1H-benzo[d]imidazol-6-amine,
6-((5-(4-(1H-pyrazol-1-yl)phenyl)-1H-pyrazol-3-yl)amino)-4-methylquinolin-2(1H)-one,
N-(5-(4-(1H-pyrazol-1-yl)phenyl)-1H-pyrazol-3-yl)-2-methyl-1H-benzo[d]imidazol-5-amine,
5-((5-(4-(1H-pyrazol-1-yl)phenyl)-1H-pyrazol-3-yl)amino)-1,3-dihydro-2H-benzo[d]imidazole-2-thione,
6-((5-(4-(1H-pyrazol-1-yl)phenyl)-1H-pyrazol-3-yl)amino)benzo[d]thiazol-2(3H)-one, or
6-((5-(4-(1H-pyrazol-1-yl)phenyl)-4-fluoro-1H-pyrazol-3-yl)amino)-3, 4-dihydroquinolin-2(1H)-one.

4. The compound of claim 3, wherein the compound is
N-(5-(4-methoxyphenyl)-1H-pyrazol-3-yl)-1H-indazol-5-amine,
6-((5-(4-hydroxyphenyl)-1H-pyrazol-3-yl)amino)-3,4-dihydroquinolin-2(1H)-one,
6-((5-(4-(1H-pyrazol-1-yl)phenyl)-1H-pyrazol-3-yl)amino)-3,4-dihydroquinolin-2(1H)-one,
5-((5-(3-fluoro-4-hydroxyphenyl)-1H-pyrazol-3-yl)amino)indolin-2-one,
6-((5-(4-(1H-imidazol-1-yl)phenyl)-1H-pyrazol-3-yl)amino)-3,4-dihydroquinolin-2(1H)-one,
N-(5-(4-(1H-pyrazol-1-yl)phenyl)-1H-pyrazol-3-yl)-1H-indazol-5-amine,
4-(3-((1H-indazol-5-yl)amino)-1H-pyrazol-5-yl)phenol,
4-(3-((1H-indazol-5-yl)amino)-1H-pyrazol-5-yl)-2-fluorophenol,
7-((5-(4-(1H-pyrazol-1-yl)phenyl)-1H-pyrazol-3-yl)amino)-2H-benzo[b][1,4]oxazin-3(4H)-one,
7-((5-(4-hydroxyphenyl)-1H-pyrazol-3-yl)amino)-2H-benzo[b][1,4]oxazin-3(4H)-one,
5-((5-(4-(1H-pyrazol-1-yl)phenyl)-1H-pyrazol-3-yl)amino)benzo[d]oxazol-2(3H)-one,
N-(5-(4-fluorophenyl)-1H-pyrazol-3-yl)-1H-benzo[d]imidazol-6-amine,
6-((5-(4-(1H-pyrazol-1-yl)phenyl)-1H-pyrazol-3-yl)amino)-4-methylquinolin-2(1H)-one, N-(5-(4-(1H-pyrazol-1-yl)phenyl)-1H-pyrazol-3-yl)-2-methyl-1H-benzo[d]imidazol-5-amine, 5-((5-(4-(1H-pyrazol-1-yl)phenyl)-1H-pyrazol-3-yl)amino)-1,3-dihydro-2H-benzo[d]imidazole-2-thione, or 6-((5-(4-(1H-pyrazol-1-yl)phenyl)-1H-pyrazol-3-yl)amino)benzo[d]thiazol-2(3H)-one.

5. A composition comprising a compound of claim 1 or a pharmaceutically acceptable salt thereof, and a pharmaceutically acceptable carrier.

6. A method for treating cancer comprising administering to a subject in need thereof a therapeutically effective amount of a compound of claim 1 or pharmaceutically acceptable salt thereof.

7. The method of claim 6, wherein the cancer is colorectal cancer, breast cancer, brain tumor, gastric cancer, liver cancer, ovarian cancer, lung cancer, gastrointestinal cancer, leukemia, or melanoma.

8. The method of claim 7, wherein the cancer is colorectal cancer.

* * * * *